United States Patent
Hober et al.

(10) Patent No.: US 11,820,802 B2
(45) Date of Patent: Nov. 21, 2023

(54) LIGAND AND USE THEREOF

(71) Applicant: Cytiva BioProcess R&D AB, Uppsala (SE)

(72) Inventors: Sophia Hober, Stockholm (SE); Sara Kanje, Stockholm (SE); Johan Nilvebrant, Taby (SE)

(73) Assignee: Cytiva BioProcess R&D AB, Uppsala (SE)

( * ) Notice: Subject to any disclaimer, the term of this patent is extended or adjusted under 35 U.S.C. 154(b) by 1242 days.

(21) Appl. No.: 16/328,058

(22) PCT Filed: Sep. 5, 2017

(86) PCT No.: PCT/EP2017/072182
§ 371 (c)(1),
(2) Date: Feb. 25, 2019

(87) PCT Pub. No.: WO2018/046475
PCT Pub. Date: Mar. 15, 2018

(65) Prior Publication Data
US 2019/0218265 A1 Jul. 18, 2019

(30) Foreign Application Priority Data

Sep. 8, 2016 (GB) ..................................... 1615254
Apr. 13, 2017 (GB) ..................................... 1705960

(51) Int. Cl.
*C07K 14/47* (2006.01)
*C07K 1/22* (2006.01)
*C07K 14/31* (2006.01)

(52) U.S. Cl.
CPC ............ *C07K 14/4728* (2013.01); *C07K 1/22* (2013.01); *C07K 14/31* (2013.01); *C07K 2319/20* (2013.01); *C07K 2319/30* (2013.01); *C07K 2319/705* (2013.01)

(58) Field of Classification Search
CPC ...... C07K 14/4728; C07K 1/22; C07K 14/31; C07K 2319/30; C07K 2319/705
See application file for complete search history.

(56) References Cited

FOREIGN PATENT DOCUMENTS

| CN | 102770764 A | 11/2012 |
|---|---|---|
| CN | 103314008 A | 11/2012 |
| CN | 103269761 A | 8/2013 |
| EP | 2762564 A1 | 8/2014 |
| GB | 2441208 A | 2/2008 |
| JP | 07-126297 A | 5/1995 |
| JP | H07126297 A | 5/1995 |
| WO | 2008/147859 A2 | 12/2008 |

OTHER PUBLICATIONS

Anna Marabotti, The misuse of terms in scientific literature, vol. 26 No. 19 2010, p. 2498.*
Phei Er Saw, Phage display screening of therapeutic peptide for cancer targeting and therapy, Protein Cell 2019, 10(11):787-807.*
Adam Zwolak, Rapid Purification of Human Bispecific Antibodies via Selective Modulation of Protein A Binding, Nature, ScienTific Reports | 7: 15521, 2017.*
Japanese Office Action for JP Application No. 2019-512905 dated May 24, 2021 (14 pages with English translation).
PCT International Search Report and Written Opinion for PCT Application No. PCT/EP2017/072182 dated Nov. 16, 2017 (14 pages).
Hentz et al., "Bifunctional fusion proteins of calmodulin and protein A as affinity ligands in protein purification and in the study of protein-protein interactions," Anal Chem. 1996, 68(22):3939-44.
Kanje, "Engineering of Small IgG Binding Domains for Antibody Labelling and Purification," 2016, https://www.diva-portal.org/smash/get/diva2:956047/FULLTEXT.pdf.
Marino et al., "Morphs' (MRFs):Metal-Reversible Folding Domains for Differential IgG Binding," Chemistry & Biology, 2001, 8:1221-1229.
Stirling et al. "Protein A-calmodulin fusions: a novel approach for investigating calmodulin function in yeast," Molecular Biology, 1992, 703-713.
First Office Action for Chinese Patent Application No. 201780055034. 2, dated Jul. 21, 2022 (22 pages with English Translation).
Nathaniel G. Hentz, et al., "Bifunctional fusion proteins of calmodulin and protein A as affinity ligands in protein purification and in the study of protein-protein interactions", Anal. Chem., vol. 68, No. 22, pp. 3939-3944.
Stephen F. Marino, et al., "Morphs (MRFs): metal-reversible folding domains for differential IgG binding" Chemistry & Biology, vol. 8, pp. 1221-1229.

* cited by examiner

*Primary Examiner* — Julie Ha
*Assistant Examiner* — Erinne R Dabkowski
(74) *Attorney, Agent, or Firm* — Eversheds Sutherland (US) LLP

(57) ABSTRACT

The present invention is within the field of protein engineering and purification. The invention relates to a target-binding polypeptide mutant of an IgG binding polypeptide, such as Protein A, Protein G, Protein L or Protein M, comprising a metal binding motif. More closely the invention relates to an Fc binding ligand comprising an engineered protein based on the Protein A derived Z domain, to which a calcium binding EF-loop has been introduced.

22 Claims, 8 Drawing Sheets
Specification includes a Sequence Listing.

a)
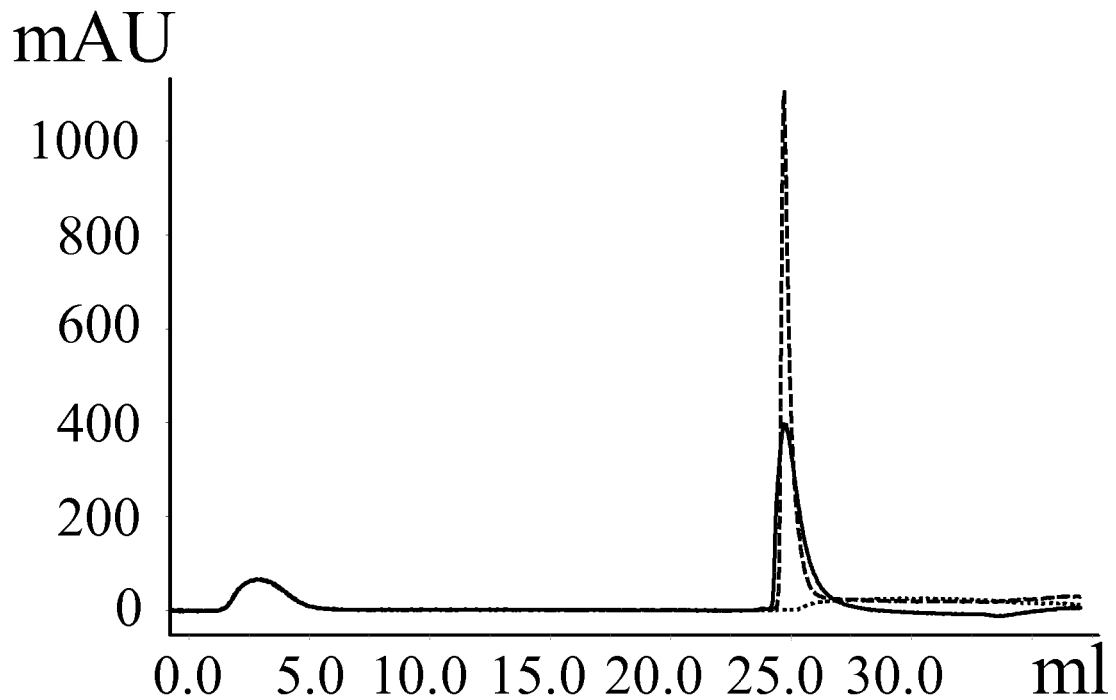
b)
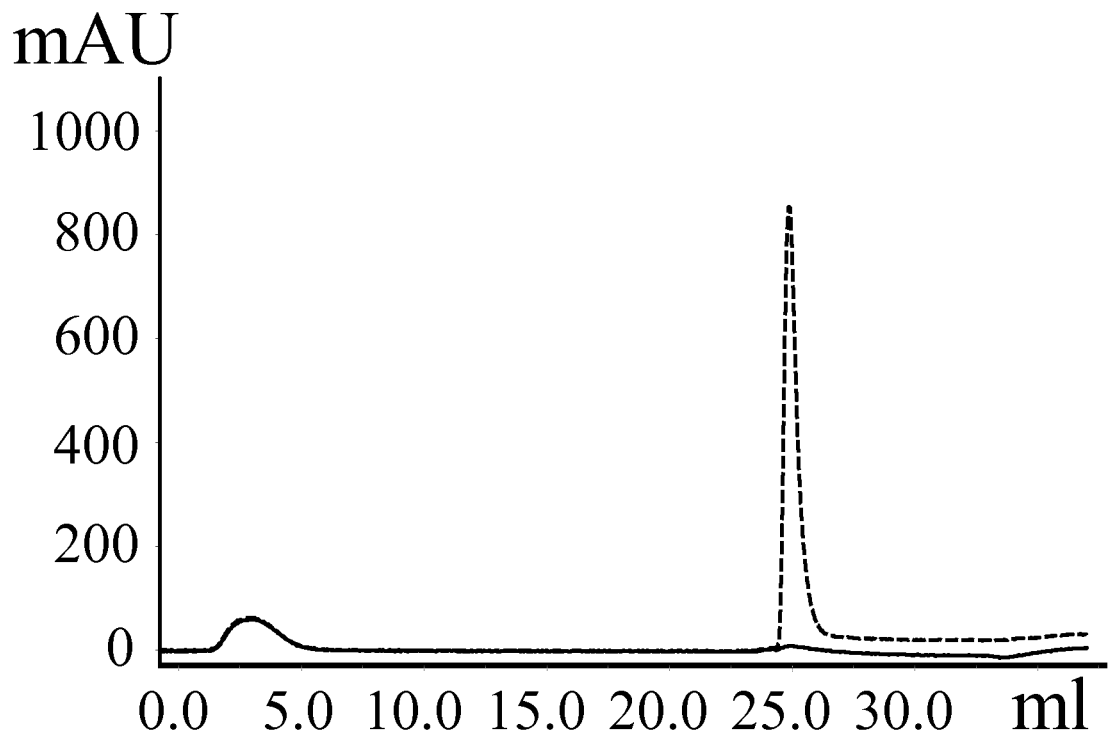
FIG 3

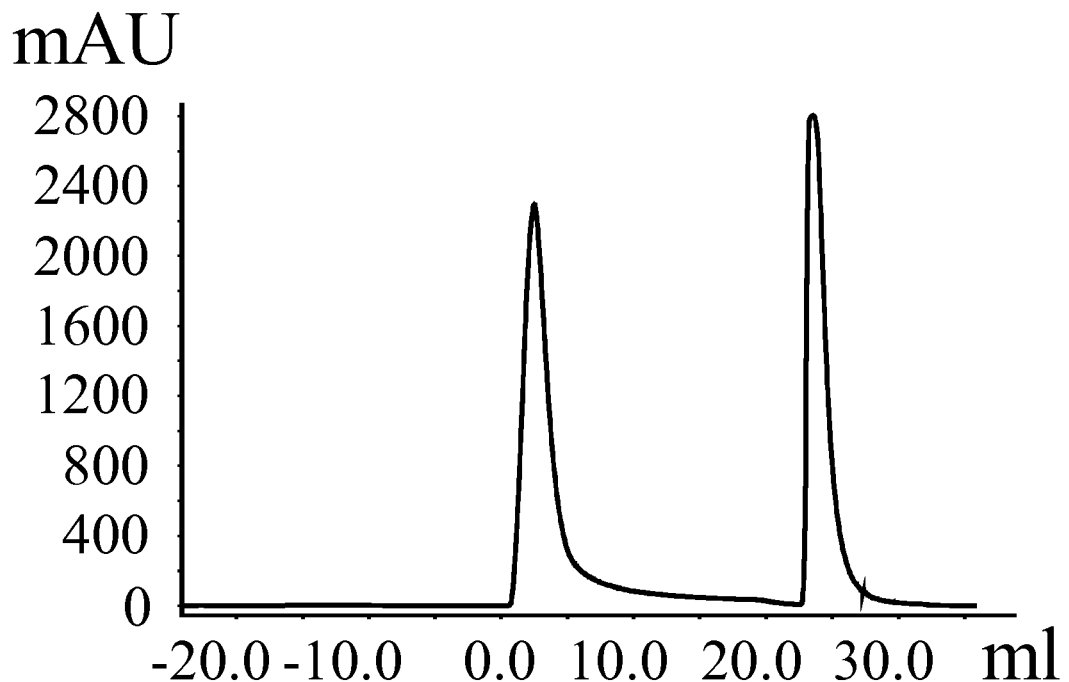
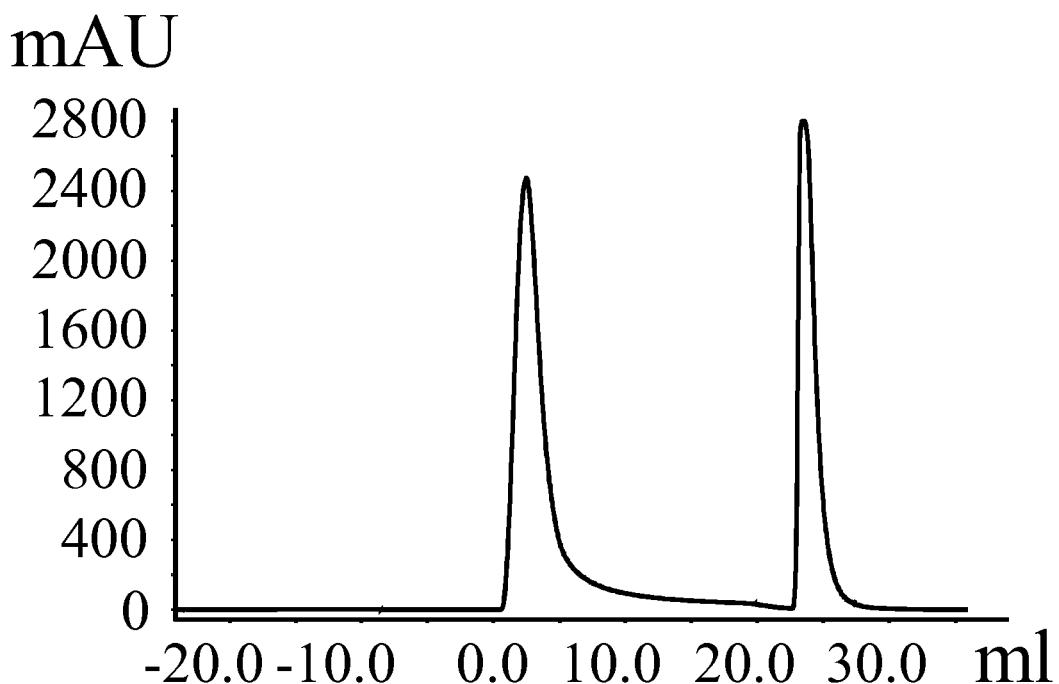
FIG 6A top, 6B bottom

LIGAND AND USE THEREOF

CROSS REFERENCE TO RELATED APPLICATIONS

This application claims the priority benefit of PCT/EP2017/072182 filed on Sep. 5, 2017 which claims priority benefit of Great Britain Application Nos. 1615254.8 and 1705960.1, filed Sep. 8, 2016 and Apr. 13, 2017, respectively. The entire contents of which are hereby incorporated by reference herein.

SEQUENCE LISTING

The instant application contains a Sequence Listing which has been submitted electronically in ASCII format and is hereby incorporated by reference in its entirety. Said ASCII copy, created on Feb. 19, 2019, is named 4147783_1.txt and is 7,291 bytes in size.

FIELD OF THE INVENTION

The present invention is within the field of protein engineering and purification. The invention relates to a target-binding polypeptide mutant of an IgG binding polypeptide, such as Protein A, Protein G, Protein L or Protein M, comprising a metal binding motif. More closely the invention relates to an Fc binding ligand comprising an engineered protein based on the Protein A derived Z domain, to which a calcium binding EF-loop has been introduced.

BACKGROUND

Antibodies are one of the most widely used reagents in the biological sciences and the therapeutic antibody field is ever increasing with world wide annual sales approaching 100 billion dollars[1]. Purification of antibodies is generally performed using Protein A based affinity chromatography[2], a simple and robust method that yields pure and concentrated product in a single purification step[3,4]. The main drawback is the need for acidic pH (3-4) for elution. Since many antibodies suffer from sensitivity to low pH, which can cause the antibody to aggregate or even lose its function[5,6], this hampers both the development and purification of new antibody based tools.

Various attempts have been made to improve the elution environment for antibodies captured on Protein A columns. Examples include binding site mutations of the Protein A derived Z domain[7] and loop engineering of the same domain[8], which could increase the elution pH to 4-4.5. Addition of urea or arginine to the elution buffer has been shown to suppress protein aggregation[6,9] and mutations that decrease the hydrophobicity of the domains of Protein A have been made, which resulted in a thermo responsive Protein A that allows elution at 40° C.[10].

One way for nature to control protein activity is by altering the three-dimensional structure. Calcium binding proteins containing the EF-hand motif are allosterically controlled by calcium ions. Upon binding to calcium, these proteins can undergo conformational changes that enable ion regulated functions[11,12]. The calcium ion is coordinated by a loop found in the EF-hand consisting of 12 amino acids, where certain positions within the protein motif have preserved amino acids while other positions are more flexible[13]. EF-loop motifs have been successfully grafted onto model proteins[14].

Metal binding has been utilised in protein engineering for purification purposes. A split calcium protein based on EF-hand subdomains has been reported that can be used as a tag and affinity handle in protein purification with a calcium dependent elution[15]. Moreover one of the antibody binding domains from Streptococcal Protein G has been engineered to contain a metal binding site causing the domain to lose its ability to bind immunoglobulin G (IgG) with a transition metal present[16].

As described above in relation to conventional Protein A chromatography, the need for acidic elution may be detrimental to the antibody or Fc-fused protein being purified. Furthermore it is known that acidic pH increases aggregation of the protein, causing lower yields. Thus, it would be desirable to have a Protein A ligand that allows elution at higher pH than prior art pH 3-4.5.

SUMMARY OF THE INVENTION

The present invention solves the above and other problems by providing an engineered protein, preferably based on the Protein A derived Z domain, to which a metal binding loop, preferably a calcium binding EF-loop has been introduced. The engineered protein domain can be used to purify antibodies with mild elution at a pH substantially higher than possible with prior art ligands. The novel ligand of the invention provides a valuable new tool for especially antibody and Fc-fusion protein purification.

In a first aspect, the invention relates to target-binding polypeptide mutant of an IgG-binding polypeptide, comprising a metal binding motif, wherein the target binding occurs in the presence of a metal ion. The IgG-binding polypeptide is preferably derived from Protein A, Protein G, Protein L or Protein M, more preferably a mutant domain of Staphylococcus Protein A (SpA).

The polypeptide mutant of the invention is preferably Fc-binding, i.e has ability to bind the Fc portion of antibodies, or part thereof comprising at least the Fc-portion, or to other proteins aggregated or fused to and Fc-portion.

In a preferred embodiment the Fc-binding mutant is a mutant of domain Z derived from SpA domain B.

The metal binding motif is preferably calcium binding, for example obtained by random mutagenesis or otherwise derived from calpain, AtcBL2 or calmodulin. According to a preferred embodiment the metal binding motif is inserted between helix 2 and 3 of the Z domain. The polypeptide mutant may comprise a linker, preferably GGG, before the metal binding motif sequence.

Preferably, the polypeptide mutant is selected from SEQ ID NO 1-9 (Zmat1-Zmat9) or a corresponding sequence comprising at least 80%, such at least 90% or 95% sequence homology with said sequences. More preferably, the polypeptide mutant comprises SEQ ID NO 8 (Zmat8) or a corresponding sequence comprising at least 80%, such at least 90% or 95% sequence homology with said sequence. The target binding portions as well as the metal binding motif are the most essential parts of the sequences 1-9 and therefore terminal linker sequences, such as 1-8 N-terminal amino acids and 1-3 C-terminal amino acids, may be deleted or selected from any other amino acids or suitable substances than those mentioned for said sequences. However, minor variations within the essential parts of the sequences 1-9 are also encompassed in the invention so long as the desired properties of the polypeptide mutant are kept.

For increased alkali stability the polypeptide mutant may comprise the following mutations in the Z domain N3A, N6D, N23T, preferably N23T. This feature is especially useful in affinity chromatography requiring alkali stable ligands.

In a second aspect, the invention relates to a ligand, or binding molecule or affinity binder comprising a polypeptide mutant as described above. The ligand may exist as a multimer, such as a dimer, trimer, tetramer, pentamer or hexamer. In cases of a multimer, amino acid residues of a signal peptide may additionally be present in the SEQ ID NO 1-9, such as SEQ ID NO 8, as well as a C-terminal cysteine.

In a third aspect, the invention relates to a chromatography matrix comprising the ligand of the invention coupled thereto. The chromatography matrix may be of natural or synthetic origin, and is preferably a polysaccharide matrix, such as an agarose matrix.

In a fourth aspect, the invention relates to a method for purification of sample proteins, comprising binding the sample proteins to a ligand or multimer thereof as described above in the presence of a metal ion; and eluting bound proteins by addition of a metal binding molecule/chelating molecule. The invention enables elution at a pH above 4.5, such as pH 5-7, preferably about pH 5.5, such as pH 5.4-5.6. The elution is preferably with a chelating agent, such as EDTA, EGTA, glutamate diacetate and citrate glutamate.

The target or sample proteins are antibodies or parts thereof, such as IgG or Fc-fusion proteins, and may be present in complex sample mixtures, such as culture supernatants.

In a fifth aspect, the invention relates to a nucleic acid or vector encoding a polypeptide selected from SEQ ID NO 1-9.

In a sixth aspect, the invention relates to an expression vector comprising the any of the above nucleic acids or vectors.

In a seventh aspect, the invention relates to use of polypeptides/proteins comprising a metal binding motif and/or multimers thereof as immobilized ligands for affinity chromatography or IMAC chromatography of His-tagged proteins.

BRIEF DESCRIPTION OF THE DRAWINGS

FIG. 4 SDS-PAGE (left) and Western Blot (right) analysis of a cell culture supernatant purification experiment on the Zmat8 column. Cell culture supernatant containing approximately 10 mg/l IgG was purified on a column coupled with Zmat8. The flow through (FT) and the eluted fractions containing proteins (E) were saved and run on an SDS-PAGE next to un-purified supernatant (S) and a molecular weight marker (M). The SDS-PAGE was transferred to a PVDF-membrane and detected with anti-human-HRP coupled antibody, detecting IgG in the supernatant and the eluate but not in the flow through.

FIG. 6 shows representative chromatograms for purification on a column with Zmat8 trimer (a) or Zmat8 tetramer (b) saturated with IgG. The IgG was eluted with EDTA at pH 5.5. The first peak shows the void at IgG injection and the second peak is eluted IgG after washing.

DETAILED DESCRIPTION OF THE INVENTION

Figure 1A:
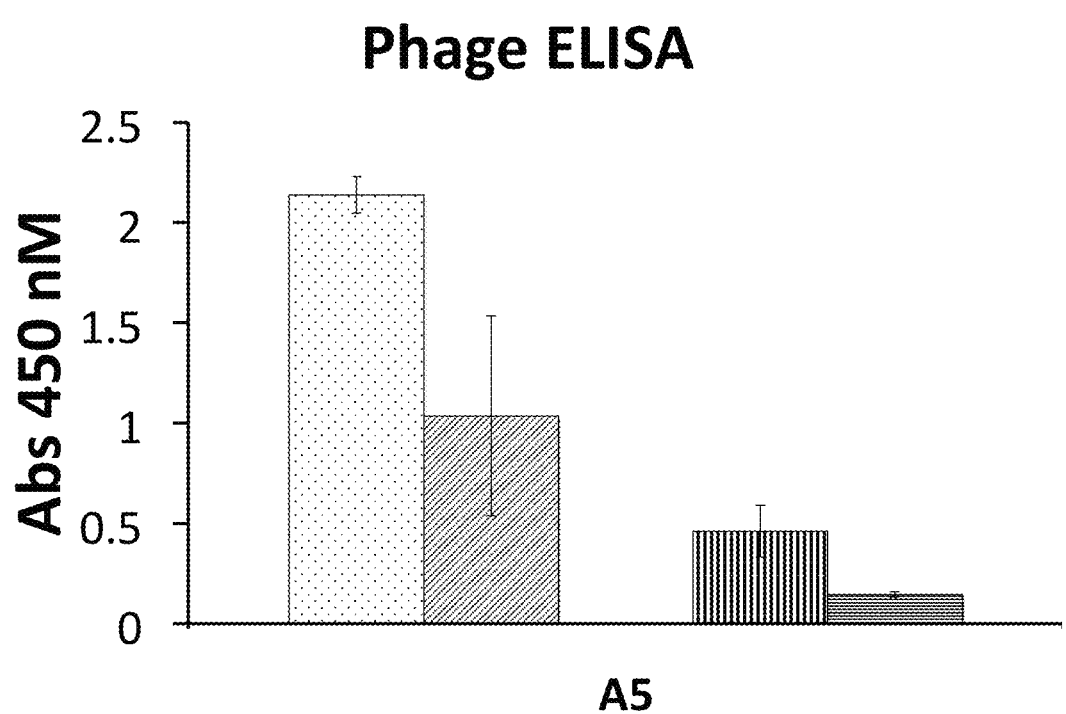
FIG. 1 a) Phage ELISA signal for variant A5 run in triplicates. The ELISA compares signal from the phage supernatant incubated in a plate coated with polyclonal IgG in presence of calcium (dots), EDTA (angled stripes), urea and calcium (vertical stripes) and urea and EDTA (horizontal stripes) respectively. b-c) Sensorgrams for 25 nM A5 (b) and 125 nM A5 (c) flown over a polyclonal IgG surface. In b) the running buffer is 1xTBST with calcium (top curve) or EDTA (bottom curve). In c) the running buffer is 1xTBST with 2 M urea and calcium (top curve) or EDTA (bottom curve). The interaction between A5 and IgG is stronger with calcium present than with EDTA.

The present invention presents a novel ligand for purification of proteins, such as antibodies, by affinity chromatography, developed from a calcium dependent IgG-binding domain. As parental scaffold, the Z domain derived from the B domain of protein A[17], has been used. This is a small three-helix bundle protein that interacts with the Fc-region of IgG with high affinity. A Z-domain library was constructed by the grafting of a randomized calcium binding loop between helix two and three of the domain. Phage display selections were performed in order to isolate protein variants exhibiting a calcium dependent binding to IgG. The final domain, denoted Zmat8, can selectively capture IgG from a complex cell culture supernatant giving a high degree of purity after a single purification step with calcium dependent elution. The achieved purity and yield are comparable to the parental Z domain.

The Z domain scaffold has also been used as a starting point for the development of variants with affinity for other targets than IgG Fc. Through randomization of the binding surface and subsequent selection against a desired target, such Z variants (Affibody® molecules) have been created and commercialized in a variety of applications. A review of the technology and its applications and nomenclature is given in Löfblom et al[34]. It is contemplated that the present invention is applicable to Z domain variants with any binding affinity, and that a metal binding motif may be introduced in such variants in a fashion similar to that described herein for IgG Fc binding polypeptides. Given that the three-dimensional structure of Z variants is considered to be conserved also when creating variants with other affinities, a calcium binding loop could for example be introduced at the corresponding position in any Z variant, and used to modulate its stability and binding properties.

The invention will now be described more closely in association with the accompanying figures and some non-limiting experiments.

MATERIALS AND METHODS

All enzymes and purification kits were used according to manufacturer's instructions. All enzymes were purchased from New England Biolabs (NEB) unless otherwise stated. Cloning PCR reactions were performed with Phusion DNA polymerase and PCR screens with Dynazyme II DNA polymerase (ThermoFisher). All PCR reactions were purified using the Qiagen PCR purification kit and gel extractions were performed with the Qiagen gel extraction kit.

Cloning
Test Variants
Single Stranded Helix One and Two

Single stranded DNA corresponding to helix one and two of Z was produced by amplification by PCR with a biotinylated forward primer containing the NdeI restriction site upstream of the 5' end of Z (SKJN1) and a reverse primer binding to the end of helix two. Streptavidin beads (Dynabeads M-270, Invitrogen) were washed twice with binding buffer (2 M NaCl, 10 mM Tris-HCl, 1 mM EDTA, 0.1% Tween20, pH 7.6) and dissolved in binding buffer. 20 µl washed beads were mixed with 20 µl PCR-product and incubated 2 h with rotation at room temperature (RT). The beads were washed in 50 µl 1xSCC (0.15 M NaCl, 15 mM sodium citrate, pH 7.0) and resuspended in 20 µl 0.15 M NaOH. The supernatant containing the non-biotinylated DNA-strand was discarded. The single stranded biotinylated 5'-3' DNA was dissociated from the streptavidin beads by incubation in 95% formamide with 10 mM EDTA, 90° C. for 2 min. The single stranded DNA was precipitated by addition of 1/10 volume of NaAc (3 M, pH 5.2) and 3x volume 95% EtOH.

The reaction was incubated overnight at −20° C. followed by centrifugation at 14 000 xg for 30 min. The supernatant was discarded and the pellet was washed with 70% EtOH followed by 15 min centrifugation at 14 000xg. The supernatant was discarded and the pellet let dry. After drying it was dissolved in 10 µl 1xTE (10 mM Tris, 1 mM EDTA).

Annealing and Extension With Loop and Helix Three

The single stranded DNA of helix one and two (5 pmol) was mixed with a reverse primer (5 pmol) encoding part of helix three, the calmodulin loop, a 18 bp overlap with the 3' end of helix two and in some cases a linker upstream of the loop. A standard PCR reaction was run for six cycles after which 2.5 pmol of SKJN1 and a reverse primer annealing to helix three containing the NheI restriction site were added and the PCR was run for an additional 50 cycles.

Cleaving and Ligation

The purified Z-loop constructs as well as the pET-26b(+) vector (T7 promoter, kanamycin (Km) resistance, Novagen) containing the original Z construct were cleaved with NdeI and NheI restriction enzymes. The PCR fragments were purified and the vector was run on and extracted from an agarose gel.

The cleaved vector and insert were ligated with T4 ligase using a 3x excess of insert.

A5

The A5 gene was amplified from the phagemid by PCR using primers annealing to the 5' and 3' end of Z, respectively. The forward primer had an overhang containing the NcoI restriction site and the reverse primer an overhang with the AscI restriction site.

The fragment and the vector pHis[32] (T7 promoter, Km resistance) were cleaved with NcoI-HF and AscI. Purified fragment and gel-extracted vector were ligated with T4 ligase with a 5x excess of fragment.

Zmat1-9

Zmat1-9 were cloned in the same way as A5 but with specific primers matching the mutations differing from the original scaffold in the beginning and/or end of the gene.

Zmat8 Destabilised Variants

The mutations H18R, F30A and L44A were introduced to Zmat8 by a two step PCR reaction. In step one 25 pmol of a mismatch primer with the desired mutation and 25 pmol of a primer annealing to the 5' end of Zmat8 containing the NcoI restriction site were used with Zmat8 as template. In the second step (H18R and F30A only) 5 µl of the PCR product from step one was used as one primer and combined with 25 pmol of a primer binding to the 3' end of Zmat8 containing the AscI restriction site. Zmat8 was used as the template. The L44A F30A substitution was made in the same way as the L44A substitution but using Zmat8(F30A) as a template. The variants were cleaved with AscI and NcoI-HF (H18A, F30A) or NcoI-HF and NheI-HF (L44A, F30AL44A) and ligated with a 5x excess to the pHis vector, cleaved with the corresponding restriction enzymes, using T4 DNA ligase.

Library Construction
Original Library

The pAY02592 phagemid (essentially identical to pAffi1 described in[33]) was modified to contain the Z-loop gene (pAYZ-loop). The Z-loop construct was amplified with primers binding to its 5' and 3' ends with the forward primer containing the XhoI restriction site (SAKA1) and the reverse primer containing the SacI restriction site followed by the SnaBI restriction site (SAKA2). The phagemid and the Z-loop gene were cleaved with XhoI and SnaBI. The plasmid was gel extracted and dephosphorylated and the fragment was purified. The cleaved gene and plasmid were ligated with T4 DNA ligase according to the supplier's instructions with the addition of 5% PEG6000.

The two libraries (with and without GGG-linker before the loop library) were prepared separately.

Primer stocks for the library were prepared (100 pmol/µl). The forward stock contained primers encoding helix one and two with 50% of the stock encoding the F30A mutation. The reverse stock contained primers encoding an 18 bp overlap with the 3' end of helix two, linker (GGG-loop library only), the loop library and helix three. 50% of the stock encoded helix three without mutations. The other 50% had equal amounts of primers with mutations in position L44, A48, L51 or any combination of the three (L44X+A48X, L44X+L51X, A48X+L51X, L44X+A48X+L51X).

The libraries were annealed and extended by mixing 5 pmol of each library stock and extended during six cycles. 100 pmol of SAKA1 and SAKA2 was added and the library was amplified for 15 cycles followed by PCR purification.

The fragments were cleaved with SacI-HF and XhoI restriction enzymes and purified with phenol/chloroform extraction followed by ethanol precipitation according to standard procedures. The purified libraries were run on a 2% GTG agarose gel and the bands of the correct size were cut out and gel extracted.

The pAYZ-loop phagemid was cleaved and purified in the same way as the library fragments.

5 µg cleaved phagemid was ligated with 1 µg (5x excess) library fragment with T4 ligase at 16° C. over night (ON). The ligations were purified by phenol/chloroform extraction followed by ethanol precipitation. The two libraries were pooled.

The pooled libraries were transformed to ER2738 cells (Lucigen) by electroporation, 21 reactions, according to instructions. After 1 h phenotyping the transformation reactions were pooled and grown ON in 2x 500 ml Tryptic Soy Broth (TSB, 30 g/l Merck) with 100 µg/ml ampicillin (Amp) at 37° C. The cells were harvested after 16 h at 2700 xg, 15 min, 4° C. The pellets were dissolved in 40 ml 20% glycerol (final glycerol concentration 15%) aliquoted and stored at −80° C.

Maturation Library

The maturation library was made with error prone PCR using the GeneMorph II kit (Agilent) with primers annealing just upstream and downstream of the A5 gene in pAYZ-loop, respectively. Five consecutive rounds of error prone PCR with 0.1 pg template were performed. The library fragment was purified using gel extraction.

The library fragment was used in a restriction free cloning reaction in order to introduce the library into the phagemid. 50 ng pAYZ-loop containing the A5 gene was mixed with 60 ng library fragment and thermo cycled (95° C. 1 min [95° C. 50 s, 60° C. 50 s, 68° C. 9 min]x25). DpnI enzyme (1 µl) was added and incubated at 37° C., 2 h. The plasmid was purified using the Qiagen miniprep kit and electroporated to ER2738 cells.

Library Amplification 100x the library size ($2*10^{10}$ (original library) or $2*10^9$ (maturation library)) were inoculated to 100 ml TSB with 2% glucose, 100 µg/ml Amp, 10 µg/ml tetracycline (Tet) and 1 mM $CaCl_2$ and incubated at 37° C. until an $OD_{600}$ of approx. 0.5-0.8. A 10x excess of M13K07 helper phage was added and incubated at 37° C., 30 min. The culture was divided in two and centrifuged at 2500 xg, 10 min. Each pellet was dissolved in 5 ml TSB with yeast extract (5 g/l, Merck, TSB+Y). Each pellet was added to 495 ml of TSB+Y with 100 µg/ml Amp, 50 µg/ml Km, 1 mM isopropyl-β-D-thiogalactopyranoside (IPTG) and 1 mM $CaCl_2$. The cultures were incubated at 30° C., 250 rpm, ON.

Phage Precipitation

Cells were pelleted at 10 000 xg for 10 min. The supernatant was saved and ¼ of the supernatant volume of 5xPEG/NaCl (20% PEG6000, 2.5 M NaCl) was added and let incubate on ice for 1-2 h. The phages were pelleted at 10 500 xg, 30 min and the pellet was dissolved in 10 ml 1xTBS (50 mM Tris, 150 mM NaCl, pH 7.5) per 50 ml cultivation culture volume and filtered through 0.45 µm syringe filters. ¼ of the volume of 5xPEG/NaCl was added and incubated on ice for 45 min. The precipitation was centrifuged at 3500 xg 50 min and the pellet was dissolved in 1xTBSTB (1xTBS, 0.1% Tween20, 3% BSA).

Phage Titration

Phages were titrated by making a series of 1:10 dilutions in water in a microplate. 100 µl ER2738 cells in log phase were added per well and incubated 5 min. The infected bacteria (5 µl/dilution) were plated on Amp-plates (100 µg/ml) and incubated at 37° C. ON.

Selection

Negative selections were performed in EIA/RIA tubes (high binding, Greiner bio-one) coated with polyclonal human IgG (20 µg/ml) in 3 ml coating buffer (50 mM carbonate, pH 9.6) 45 min RT with rotation, followed by storage at 4° C. The tubes were blocked with 3 ml 1xTBSTB with 100 mM EDTA for 1 h at RT with rotation. Phage stock (amount in colony forming units (cfu)) was diluted in 2 ml 1xTBSTB with 100 mM EDTA and added to a blocked tube. After incubation 20 min at RT with rotation the phage mix was transferred to a new tube and incubated for 20 min.

After negative selection the remaining phage were buffer exchanged in an Amicon Ultra-0.5 ml centrifugal filter with 30 kDa cut-off (Merck). The concentrator membrane was washed with 500 µl 1xTBSTB 14 000 xg 5 min. The output from the negative selection was added 500 µl at a time and concentrated at 14 000 xg 5-10 min. The concentrated phages were washed with 1xTBST (1xTBS, 0.1% Tween20) four times. The washed phages were removed from the concentrator and diluted to a final volume of 1 ml with 1xTBSTB with 2 M urea and 5 mM $CaCl_2$ (input positive selection).

Target polyclonal IgG was biotinylated with EZ-link™ Sulfo-NHS-Biotin (ThermoFisher) according to the manufacturer's instructions.

Streptavidin coated beads (Dynabeads M-280 (Invitrogen)), washed with 1xTBST and blocked with 1xTBSTB for 30 min at RT with rotation, were used in pre- and positive selections.

The positive selection input was pre-selected against streptavidin beads and microtubes (blocked with 1xTBSTB) for 1 h with rotation at RT. The pre-selected library (supernatant) was incubated with 50 nM biotinylated IgG 2 h, RT with rotation. After target incubation the phage and target were incubated with streptavidin coated beads for 15 min at RT with rotation. The beads were washed multiple times in 1 ml 1xTBST with 2 M urea and 1 mM $CaCl_2$. After washing, the phages were eluted with 500 µl 1xTBSTB with 2 M urea and 100 mM EDTA, 5 min, RT with rotation. The supernatant was saved and diluted with 450 µl 1xTBST and 50 µl 1 M $CaCl_2$.

After selection the eluate (750 µl after the first round, 500 µl for all following rounds) was amplified by infecting 5 ml ER2738 cells in early log-phase ($OD_{600}$ 0.5-0.8) still at 37° C. Amp was added to a final concentration of 100 µg/ml and the cells were incubated at 37° C., 1 h, 150 rpm. A 5x excess of M13K07 helper phage was added and incubated at 37° C., 30 min. The cells were pelleted at 3000 xg 15 min and re-suspended in 5 ml TSB+Y. This was followed by amplification in 200 ml TSB+Y with Amp (100 µg/ml), Km (25 µg/ml), $CaCl_2$ (1 mM) and IPTG (0.1 mM) in 30° C. ON. The phages were precipitated as previously described.

Sequencing

Constructs were screened with PCR followed by a single primer cycle sequencing reaction with Big Dye (Life technologies). All sequencing was performed on a 3730xl DNA analyser (AME bioscience).

Phage ELISA

Colonies from the output titration were inoculated in 96 well deep-well plates in 500 µl TSB+Y with Amp (100 µg/ml), Tet (10 µg/ml) and $CaCl_2$ (1 mM). The plates were incubated at 37° C., 250 rpm ON. 30 µl of overnight culture was added to 720 ml TSB+Y with Amp, Tet and $CaCl_2$ and incubated at 37° C., 250 rpm, 2 h. To each well 100 µl TSB+Y with Amp, Tet, $CaCl_2$ and $10^9$ M13K07 helper phage was added and let infect at 37° C., still for 30 min. 150 µl of TSB+Y with Amp, Tet, $CaCl_2$, Km (250 µg/ml) and IPTG (0.7 mM) was added to each well and the plates were incubated at 30° C., 250 rpm ON. The phage cultures were harvested at 3000 xg 15 min and the supernatants were saved.

Non-treated 96-well half-area plates (Corning) were coated with polyclonal human IgG 1 µg/ml in 1xTBS, 50 µl/well at 4° C. ON.

Each phage supernatant was subjected to two ELISA experiments, one where all buffers contained 100 mM EDTA and one where all buffers contained 1 mM $CaCl_2$. Phage displaying the original Z scaffold was used as positive control and phage displaying a non-IgG binder was used as a negative control.

The plates were blocked with 0.5% casein in 1xTBS, 140 µl/well, 2 h RT with low shaking speed. Phage supernatants were diluted 1:20 in 0.5% casein and left 30 min at RT. Diluted phages, 50 µl/well were added to two plates and incubated 1 h at RT with low shaking. The plates were washed with 1xTBST (0.1% Tween20), 3x10 min still, 140 µl/well followed by incubation with anti-M13-HRP antibody (GE Healthcare) diluted 1:5000 in 0.5% casein, 1 h at RT with low shaking. The plates were washed as described above and developed with 50 µl TMB substrate (Pierce) 15-30 min before stopping the reaction with 50 µl 2 M $H_2SO_4$. The absorbance was read in a Sunrise™ micro plate reader (Tecan) at 450 nM.

Protein Production, Purification and Analysis
Expression

Selected variants were sub cloned to an expression vector and transformed to BL21 (DE3) cells (Novagen®, Merck4Biosciences). Single colonies were inoculated to 5 ml TSB+Y with Km (50 µg/ml) and grown at 37° C. ON at 150 rpm. Cultivations were started by adding 1 ml overnight culture to 100 ml TSB+Y with Km (50 µg/ml) and $CaCl_2$ (1 mM) and grown at 37° C. 150 rpm until $OD_{600}$ reached 0.8-1. Cultures were induced with IPTG (1 mM) and grown at 25° C. ON. The cultures were harvested at 2400 xg, 8 min at 4° C. followed by resuspension of the pellet in 5 ml 1xTBST-C (1xTBS, 0.05% Tween20, 1 mM $CaCl_2$). Resuspended pellets were diluted to 10 ml with 1xTBST-C and sonicated at 40% amplitude 1.0/1.0 s pulsing for 1 min and 30 s using a Vibra-cell (Sonics). The lysed cells were pelleted at 35 000 xg, 20 min at 4° C. after which the supernatants were saved for purification.

Purification

Columns packed with 4 ml IgG-Sepharose 6 Fast Flow (GE Healthcare) were washed with 20 ml $dH_2O$, 20 ml 0.3 M HAc (pH 3.2) and 20 ml 1xTBST-C. The columns were pulsed with 10 ml 0.3 M HAc followed by equilibration with 50 ml 1xTBST-C. The cell lysates were added followed by washing with 75 ml 1xTBST-C. The columns were washed with 50 ml 5 mM $NH_4Ac$ with 1 mM $CaCl_2$ (pH 5.5) prior to elution with 0.3 M HAc in 15x 1 ml fractions. The fractions with the highest absorbance at 280 nm were freeze-dried, dissolved in 1xTBS with 1 mM $CaCl_2$ and concentrations determined using BCA (Pierce).

Mass Spectrometry

Molecular weight was determined using matrix-assisted laser desorption ionization mass spectrometry (MALDI-MS) by mixing 1:1 with α-Cyano-4-hydroxycinnamic acid (5 mg/mL, Bruker), spotted on a MALDI-target and analysed with a MALDI-TOF LT3 plus (SAI) or a 4800 MALDI TOF/TOF Analyzer (Applied Biosystems). Electrospray ionization (ESI)-MS was also used where the samples were desalted on a C4 column (µ-Precolumn Cartridge Acclaim PepMap300 C4, 5 µm, 300A, 300 µm i.d. x 5 mm, Dionex) and analysed on an Agilent 6520 ESI Q-TOF system.

SDS-PAGE

Protein purity was determined with SDS-PAGE by mixing the protein sample with reducing buffer to a final concentration of 20 mM Tris-HCl, 1 mM EDTA, 88 mM SDS, 720 mM β-mercaptoethanol, 17% glycerol and heated for 5 min at 95° C. Reduced samples were run on a Mini-PROTEAN® TGX™ gel (Bio-Rad) in 1xTGS running buffer (Bio-Rad) at 200 V, 30 min, 4° C. The gel was washed 3x5 min in $dH_2O$ followed by staining with GelCode® Blue (Thermo scientific) for 1 h. The gel was destained in $dH_2O$ overnight. The marker used was LMW-SDS marker kit (GE Healthcare).

Western Blot

For Western blot analysis the SDS-PAGE was run on a NuPAGE Novex 4-12% Bis-Tris gel (Invitrogen) using 1xMES (50 mM MES, 50 mM TRIS, 1 mM EDTA, 0.1% SDS, pH 7.3) as running buffer. Transfer to a 0.45 µm Invitrolon PVDF Western blot membrane (Invitrogen) was performed in 1xTransfer buffer (25 mM Bicine, 25 mM BisTris, 1 mM EDTA, 10% Ethanol, pH 7.2) at 40 V for 90 min with PageRuler™ Plus Prestained Protein Ladder (Thermo Scientific) as the molecular weight marker. Blocking was performed 1 h at RT with blocking buffer (5% milk powder, 0.5% Tween20). Human antibody was detected with HRP coupled goat-anti-human antibody (Novex) at a 1:5000 dilution in blocking buffer 1 h at RT. Washing was preformed with 1xPBST (10 mM phosphate, 0.15 M NaCl, 0.1% Tween20, pH 7.4), 4 x 5 min followed by an Immobilon Western Chemiluminescent HRP substrate (Merck) readout on a BioRad ChemiDoc™ XRS+system.

CD

All CD measurements were performed on a Jasco J-810 spectropolarimeter. CD spectra were measured from 250-195 nm with a 0.1 cm cell length at a scanning speed of 100 nm/min and a data pitch of 0.1 nm. Protein melting curves were measured between 20-90° C. at 221 nm with a 5° C./min temperature ramp.

Pre study: The proteins were diluted to 0.4 mg/ml in 1xPBS (1xPBST without tween) with 100x molar excess of EDTA or $CaCl_2$, respectively. First selection: A5 was diluted to 0.2 mg/ml in 1xTBS with 1 mM $CaCl_2$ or 3 mM EDTA or 1xTBS with 1 M urea and 1 mM $CaCl_2$ or 3 mM EDTA. Maturation selection: Zmat1-9, Z or A5 were diluted to 0.2 mg/ml in 1xTBS with 1 mM $CaCl_2$ or 3 mM EDTA.

SPR
Test Variants

The test variants were run on a ProteOn™ XPR36 instrument (Bio-Rad). A GLM sensor chip was activated using standard amine coupling procedures. Monoclonal human IgG was injected at 10 µg/ml diluted in NaAc pH 4 to reach an immobilisation level of 5000 RU. The surfaces were deactivated with ethanolamine and regenerated with 10 mM HCl. The pre study variants were diluted to 300, 100, 33, 11, 3.7 and 0 nM in running buffer and injected at 50 µl/min with 330 s association and 3000 s dissociation times. All proteins were run with 1xPBST (0.05% Tween20), 1xPBST with 30 µM $CaCl_2$ and 1xPBST with 30 µM EDTA. Buffer subtracted data were fitted to a 1:1 Langmuir isotherm using the ProteOn Manager software version 3.1.0.6.

First Selection

The A5 protein was run on a Biacore 3000 instrument (GE Healthcare). Polyclonal human IgG was immobilised by amine coupling to a CM5 chip surface to 4000 RU using 1xPBST as running buffer. The A5 protein was diluted to 200, 100, 50, 25 and 12.5 nM in 1xTBST (0.05% Tween20) with 1 mM $CaCl_2$ or 100 mM EDTA and injected at 50 µl/min with a 180 s association and 420 s dissociation. The surfaces were regenerated using 10 mM HCl 30 µl/min 30 s. A5 was also injected in the same running buffers but with the addition of 2 M urea and was then diluted to 1000 nM, 500 nM, 250 nM, 125 nM, 62.5 and 0 nM.

Maturation Selection

The maturation variants (Zmat1-9), A5 and the original Z domain were analysed on a Biacore T200 (GE Healthcare).

Polyclonal human IgG and monoclonal human IgG1 was immobilised on a CM5 chip to 4000 RU by amine coupling with 1xPBST as running buffer. The proteins were diluted in 1xTBST with 1 mM CaCl$_2$ or 100 mM EDTA and run with single cycle kinetics at 50 µl/min with 180 s association and 420 s dissociation. Regeneration was done with 10 mM HCl at 30 µl/min, 30 s. The original Z domain was run at 25, 12.5, 6.25, 3.13, 1.56 and 0 nM in both buffers. A5, Zmat1-3, Zmat5 and Zmat7-9 were run at 100, 50, 25, 12.5, 6.25 and 0 nM in the calcium containing buffer and at 1000, 500, 250, 125, 62.5 and 0 nM in the EDTA containing buffer. Zmat4 and Zmat6 were run at 400, 200, 100, 50, 25 and 0 nM in the calcium containing buffer and 4000, 2000, 1000, 500, 250 and 0 nM in the EDTA containing buffer.

Purification Test IgG Sepharose

Approximately 600 µl IgG Sepharose 6 Fast Flow (GE Healthcare) was packed in a NAP-5 column. The column was pulsed with 2 ml 0.3 M HAc (pH 3.2) and 2 ml 1xTBST-C twice. 100 µg of protein diluted to 1.2 ml in 1xTBST-C was added to the column followed by a wash with 6 ml 1xTBST-C. The protein was tested for elution with 8x200 µl 100 mM NH$_4$Ac with 100 mM EDTA (pH 5, 5.7, 6, 6.5 or 7). A control experiment with the same elution buffer at pH 5 but with 1 mM CaCl$_2$ instead of EDTA was also performed. After the first elution the column was washed with 1.2 ml 5 mM NH$_4$Ac with 1 mM CaCl$_2$ at pH 5.5 followed by elution in 8x200 µl fractions with 0.3 M HAc, pH 3.2. All eluted fractions were collected in a 96-well UV Star® Microplate (Greiner bio-one) and their absorbance at 280 nM were measured in a CLARIOStar (BMG Labtech) plate reader.

Purification Test Zmat8 and Z Column

Zmat8 and Z were cloned, produced and purified as described above. 10 mg of each protein was coupled to 1 ml HiTrap™ NHS-Activated HP columns (GE Healthcare) according to the manufacturer's instructions with a coupling pH of 6.5 and a coupling time of 30 min.

Purifications of pure polyclonal human IgG, spiked Chinese Hamster Ovary (CHO) cell supernatant (100 mg/l polyclonal human IgG) and real CHO cell supernatant (monoclonal human IgG ca 10 mg/l) were performed on an Äkta Explorer system (GE Healthcare) with a flow rate of 1 ml/min. Pulsing of the columns was done with 6 column volumes (CV) 1xTBST-C followed by 6 CV elution buffer (0.3 M HAc pH 3.2 or 100 mM NH$_4$Ac, 100 mM EDTA pH 5.5 or 100 mM NH$_4$Ac 1 mM CaCl$_2$ pH 5.5). Equilibration was done with 13 CV 1xTBST-C prior to sample injection using a 2 ml sample loop. Washing was performed with 13 CV 1xTBST-C followed by 5 CV 5 mM NH$_4$Ac, 1 mM CaCl$_2$, pH 5.5. Protein was eluted with 6 CV elution buffer and collected in 0.5 ml fractions. Regeneration was done with 3 CV elution buffer and 6 CV 1xTBST-C.

EXPERIMENTAL SECTION

Determination of Loop Position

To find the best position for the introduction of a calcium binding loop in the Z domain, the structures of different calcium binding proteins and the Z domain were investigated. The distances between the N-terminus and C-terminus of calcium binding loops of calmodulin ([18], 6.6 Å), the calpain domain ([19], 7.3 Å) and the AtCBL2 protein ([20], 6.6 Å) with calcium bound were measured as well as the corresponding distance in the Apo-form of the calmodulin loop ([21], 9.6 Å, [22], average 12 Å, [23], 9.0 Å). These distances were compared to the distance between the N- and C-termini of the loops between helices one and two (average 12 Å), and two and three (average 7 Å) of the Z domain [24]. As the distance between the N- and C-terminus of the loop between helix two and three of the Z domain (7 Å) matched well with the distance in the calcium bound form of the different calcium binding loops (6.6-7.3 Å), at the same time as differing from the non-bound form of the calmodulin loop (9-12 Å), the calcium binding loop was introduced between helix two and three of the Z domain.

Grafting of Calcium Binding Loops

In order to investigate the structural and functional dependence of the loop between helix two and three, one of the calcium binding loops from calmodulin was grafted onto the Z domain. The loop between helix two and three of the Z domain (amino acid sequence: DPSQ) was exchanged for the calmodulin loop (amino acid sequence: DKDGDGTIT-TKE, SEQ ID NO 11). The effect of adding linkers before and after the loop was also investigated. Glycine and serine residues are commonly used as linkers and leucine was added to investigate the effect of a hydrophobic residue N-terminally of the loop. Therefore six variants were designed and investigated: adding the loop only (Z-loop), adding a Leu residue N-terminally of the loop (Z-Leu-loop), adding three glycines or serines N-terminally of the loop (Z-GGG-loop, Z-SSS-loop) and adding three glycines or serines N- and C-terminally of the loop (Z-GGG-loop-GGG, Z-SSS-loop-SSS). The variants as well as the original Z domain were produced and purified to homogeneity by IgG affinity chromatography. Proteins were analysed using circular dichroism (CD) for secondary structure content and melting temperature in 1xPBS, 1xPBS with 100x molar excess CaCl$_2$ and 1xPBS with 100x molar excess ethylenediaminetetraacetic acid (EDTA), respectively. The variants' interaction with monoclonal human IgG was investigated using surface plasmon resonance (SPR) with the same running buffers as used in the CD experiments complemented with 0.05% tween20. The sensorgrams showed interaction with immobilised IgG regardless of running buffer, although the data with calcium and EDTA in the buffers could not be used for kinetic analysis. The Z domain's affinity to IgG was decreased by the mere introduction of a calmodulin loop. Introducing a leucine N-terminally of the loop provided structural stabilisation of the domain and this resulted in a recovered affinity for IgG. Having glycine or serine linkers N- and C-terminally of the loop caused the largest difference in affinity for IgG compared to the Z domain. Z-loop and Z-GGG-loop were chosen for further work since they showed the largest differences in melting temperature between the calcium- and EDTA-containing buffers and displayed approximately 10-fold lower affinities to IgG compared to the original Z domain, which indicated calcium-dependent stability.

Library Design

In an effort to generate variants with more pronounced calcium dependency a combinatorial phagemid library was designed built on the two variants Z-loop and Z-GGG-loop. Based on sequences of a large number of calcium-binding loops[13, 25] degenerate codons were chosen to cover a large diversity of canonical EF-hand loops. Structurally destabilising mutations were included in the library design by changing positions 30, 44, 48 and 51[26-28] in order to make the three-dimensional structure of the Z-domain, and thereby the capability to bind to IgG, more dependent on the conformation of the calcium-binding loop. In position 30, only the substitution F30A was included aside from the original phenylalanine. For positions 44, 48 and 51 the codon KBG that encodes Ala, Gly, Leu, Ser, Trp and Val was used. The library was designed to, in addition to the library in the calcium binding loop, include 50% "wild type" Z scaffold and 50% with additional substitutions, either in position 30, 44, 48, 51 or a combination of two or several of these. In theory, the size of each library (Z-loop-lib and Z-GGG-loop-lib) was 2*10$^8$. The final library, with both sub-libraries pooled, had a size of 2*10$^8$ after transformation, which corresponds to half of the theoretical size.

First Selection

Four rounds of selection were performed to select desired variants from the library. Each round started with a negative selection towards IgG where the library was incubated in presence of EDTA to remove variants that bound under such conditions. The supernatant that included all variants that were unable to bind IgG in the presence of EDTA was buffer exchanged to a calcium containing buffer and used in positive selection. All positive selections were carried out with a surplus of target (polyclonal human IgG) compared to amount of added phages. An increasing number of washes were performed and 2 M urea was present in all steps in order to further structurally destabilise the phage displayed library members. Elution of the phages was done with EDTA. Following four rounds of negative and positive selection, the output was screened using phage enzyme-linked immunosorbent assay (ELISA) where binding to IgG in presence of calcium or EDTA, respectively, was measured. Out of 282 screened phage supernatants, one clone denoted A5, showed a large difference in binding to IgG in the presence of calcium or EDTA (FIG. 1a).

Figure 1B:
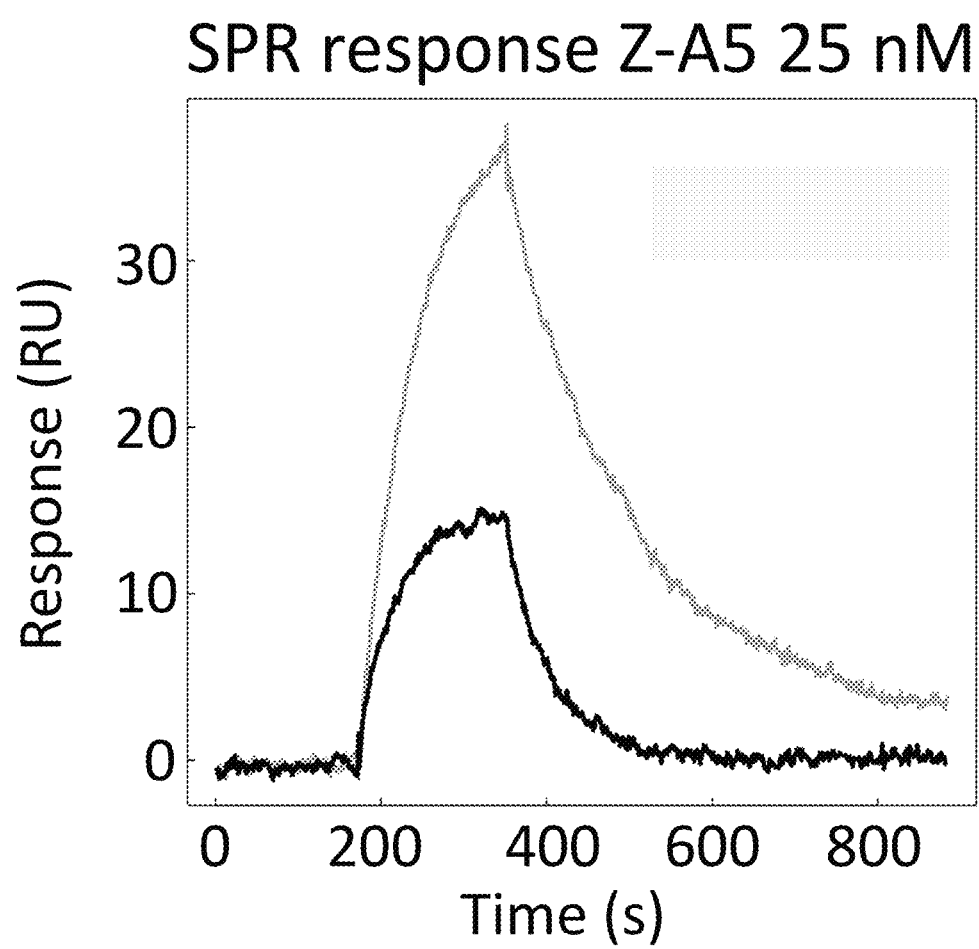
Figure 1C:
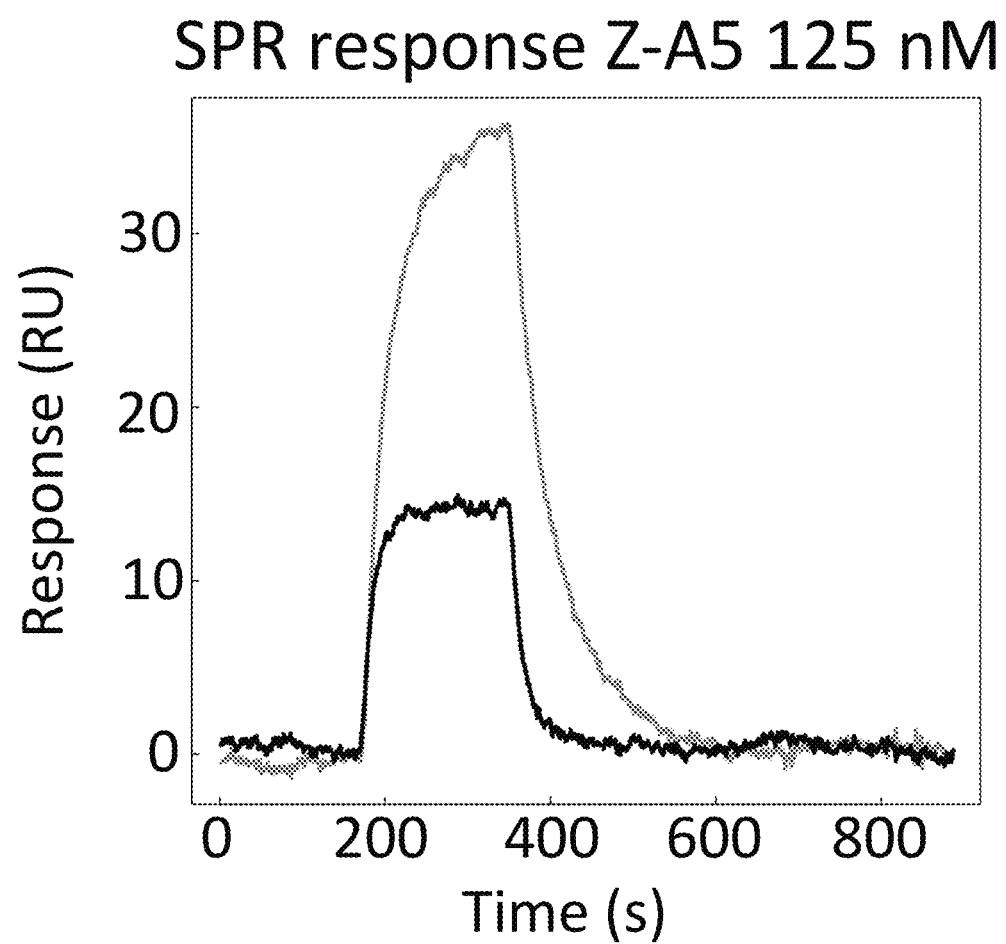

Clone A5 was sequenced, SEQ ID NO 10, and cloned into an expression vector in order to produce soluble protein. The sequence contained the GGG-linker N-terminally of the loop integrated in the original Z scaffold. The protein was expressed in bacteria and purified to homogeneity on IgG Sepharose. Purity and molecular weight were confirmed by sodium dodecyl sulphate-polyacrylamide gel electrophoresis (SDS-PAGE) and mass spectrometry (MS), respectively. The purified domain was evaluated by SPR for its affinity towards IgG in presence of calcium or EDTA with or without urea present in the buffer. The dissociation equilibrium constant ($K_D$) of A5 to IgG was 20 and 50 nM with calcium or EDTA, respectively, and 170 and 330 nM with 2 M urea and calcium or EDTA, respectively. Sensorgrams from the same concentration of protein in different running buffers injected over the same ligand surface are shown in FIG. 1b and c to visualise differences in signal and curvature. It is clear that the dissociation with EDTA present in the running buffer is much faster than with the calcium containing running buffer. Also the achieved binding signal was higher with calcium present.

The secondary structure as well as the melting temperature, in presence of calcium or EDTA, with and without urea, were analysed with CD as well as the refolding ability after thermal denaturation. The protein A5 was able to refold after melting regardless of buffer. The melting temperature differed three to four degrees between buffers with EDTA or calcium. From the CD spectra showing secondary structure it appears that A5 has higher alpha helical content when calcium is present in the buffer as compared to EDTA. Taken together these data suggest that variant A5 displays a calcium dependent difference in affinity for IgG and secondary structure content. However, the affinity for IgG with EDTA present was still too high for efficient elution by EDTA-mediated calcium depletion in a column purification setup.

Maturation Library

As the first selection resulted in only one interesting sequence, functionally important residues could not be identified through sequence alignment of selected clones. Therefore, a maturation library was made with error prone PCR using A5 as a template. The aim was a library with on average two or three random amino acid mutations per gene. The final library size was 2*10$^7$ with an expected mutation frequency based on sequencing of >250 clones.

Maturation Selection

Figure 2:
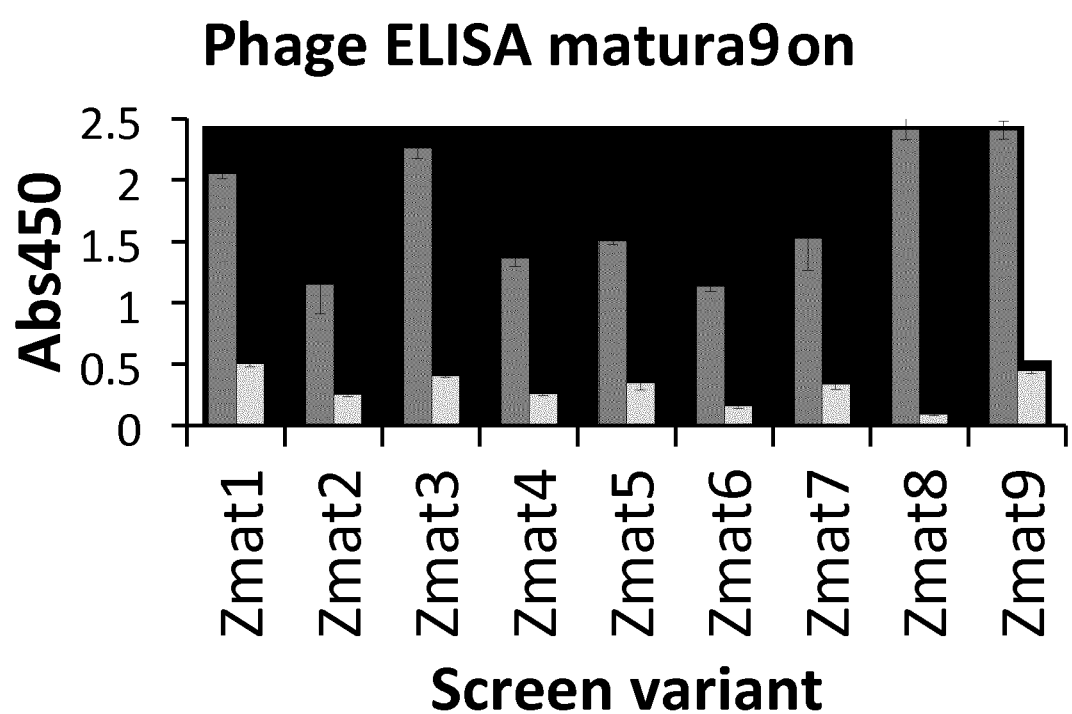
FIG. 2 Signal readout from phage-ELISA for the top nine unique variants from the maturation selection. ELISA plates coated with IgG were subjected to phage supernatant in presence of calcium (dark grey) or EDTA (light grey). After washing with calcium- or EDTA-containing buffer, bound phages were detected with anti-M13-HRP antibody. The signal readout is plotted on the y-axis. All nine variants show large differences between calcium- and EDTA-containing buffers, as well as low signals with EDTA present FIG. 3 Abs280 chromatogram from purifications of polyclonal human IgG on columns coupled with Zmat8 (a) and the Z domain (b). a) IgG was eluted from the Zmat8 column by lowering the pH to 3.2 (long dash) or by EDTA at pH 5.5 (solid) but not at pH 5.5 with calcium (grey), demonstrating a calcium-dependent elution of IgG by Zmat8. b) IgG was eluted from the Z column by lowering the pH to 3.2 (long dash) but not by EDTA at pH 5.5 (solid).

The second selection was performed in three parallel tracks. Similarly to the first selection strategy, the first step was a negative selection where the library was subjected to polyclonal human IgG in an EDTA containing buffer. This was followed by a positive selection where the supernatant with all unbound variants from the negative selection were exposed to a surplus of target compared to phages in presence of calcium. Following washing, phages that eluted upon addition of EDTA were recovered. In one track 2 M urea was present in all positive selection rounds. In the second track the amount of urea was decreased over the positive selections and in the third track no urea was present. The output from the three tracks (192 clones per track) was screened with phage-ELISA comparing binding to IgG in presence of calcium or EDTA, respectively. The most promising candidates were reanalysed in triplicates and the results from the top nine unique candidates are presented in FIG. 2.

The top nine variants (Zmat1-Zmat9) were sequenced SEQ ID NO:s 1-9. They all have substitutions in positions described to participate in the IgG binding (F5, H18, N28, Q32 and K35)[24,29,30]. Additionally, some variants (Zmat1-3) have a Gly to Ser mutation in the linker before the loop. Only one of the variants (Zmat3) has a mutation in the calcium-binding loop compared to A5.

Zmat1-9 were produced and purified to homogeneity, which was confirmed by SDS-PAGE, and molecular weights were confirmed by MS. The domains were analysed regarding secondary structure and IgG-binding and compared to the original Z domain and the parental A5 variant. The variants' affinity towards IgG in presence of calcium or EDTA, respectively, was measured by SPR. Secondary structural content, melting temperature and ability to refold after melting were investigated by CD in the same conditions. All variants were able to refold after melting. A summary of the experiments is presented in table 1.

TABLE 1[1]

Summary of the ELISA, SPR and CD results for the top nine affinity maturation variants (Zmat1-Zmat9) as well as the original Z and the parent clone AS.

| | ELISA | | | SPR | | | CD | | |
|---|---|---|---|---|---|---|---|---|---|
| Variant | Signal ELISA CaCl$_2$ (A.U.) | Signal ELISA EDTA (A.U.) | Signal ELISA CaCl$_2$/EDTA | $K_D$ CaCl$_2$ (M) | $K_D$ EDTA (M) | $K_D$ EDTA/ $K_D$ $_{CaCl2}$ | Tm CaCl$_2$ (° C.) | Tm EDTA (° C.) | ΔTm (° C.) |
| Z | 2.47 | 2.68 | 0.92 | 6.1E−09 | 3.3E−09 | 0.54 | 73 | 73 | 0 |
| A5 | 2.14 | 1.03 | 2.08 | 1.9E−08 | 5.2E−08 | 2.7 | 51 | 47 | 4 |
| Zmat1 | 2.06 | 0.51 | 4.04 | 3.9E−08 | 2.5E−06 | 63 | 56 | 46 | 10 |

TABLE 1[1]-continued

Summary of the ELISA, SPR and CD results for the top nine affinity maturation variants (Zmat1-Zmat9) as well as the original Z and the parent clone AS.

| | ELISA | | | SPR | | | CD | | |
|---|---|---|---|---|---|---|---|---|---|
| Variant | Signal ELISA CaCl$_2$ (A.U.) | Signal ELISA EDTA (A.U.) | Signal ELISA CaCl$_2$/EDTA | K$_D$ CaCl$_2$ (M) | K$_D$ EDTA (M) | K$_D$ EDTA/ K$_D$ $_{CaCl2}$ | Tm CaCl$_2$ (° C.) | Tm EDTA (° C.) | ΔTm (° C.) |
| Zmat2 | 1.15 | 0.26 | 4.42 | 6.6E−08 | 1.2E−05 | 180 | 62 | 52 | 10 |
| Zmat3 | 2.26 | 0.41 | 5.51 | 8.6E−08 | ND | ND | 52 | 43 | 9 |
| Zmat4 | 1.37 | 0.26 | 5.27 | 2.7E−06 | 9.3E−06 | 3.4 | 48 | 43 | 5 |
| Zmat5 | 1.51 | 0.35 | 4.31 | 8.1E−08 | 1.7E−06 | 21 | 55 | 50 | 5 |
| Zmat6 | 1.13 | 0.16 | 7.06 | 2.2E−07 | ND | ND | 46 | 39 | 7 |
| Zmat7 | 1.53 | 0.34 | 4.50 | 8.2E−08 | 3.7E−06 | 45 | 55 | 50 | 5 |
| Zmat8 | 2.41 | 0.1 | 24.1 | 4.3E−07 | ND | ND | 50 | ND | ND |
| Zmat9 | 2.41 | 0.45 | 5.36 | 6.0E−08 | 7.8E−07 | 13 | 51 | 47 | 4 |

[1]A.U. (absorbance units), K$_D$ (Dissociation equilibrium constant), Tm (structural melting temperature), ND (could not be determined), Purification Experiments
Experiment 1

Based on the results from phage ELISA, SPR and CD, with emphasis on the differences that were detected with and without calcium, it was decided to further investigate Zmat1 (SEQ ID NO 1), Zmat3 (SEQ ID NO 3), Zmat6 (SEQ ID NO 6) and Zmat8 (SEQ ID NO 8) in a purification setup. A fixed amount of protein (100 μg) was loaded on an IgG Sepharose column to investigate whether the protein variants could be eluted using EDTA. Additional factors investigated were the addition of 1 M urea in the elution buffer, elution at elevated temperature (37° C.) and incubation with elution buffer for 30 minutes before final elution. As a control, the EDTA elution was followed by traditional elution at pH 3.2 to collect residual protein from the column. It was concluded that the original Z domain could only be eluted at pH 3.2 while Zmat8 could be eluted in a calcium-dependent manner if the pH of the buffer was lowered to 5. The eluted peaks were analysed by SDS-PAGE. To further characterise the behaviour of Zmat8, a stepwise increase of the pH of the elution buffer (pH 5.5, 5.7, 6, 6.5 and 7) was investigated where Zmat8 was shown to be eluted with EDTA at pH 5.5 but not when increasing the pH further.

The sequence of Zmat8 is shown in SEQ ID NO 8. It contains three amino acid substitutions in helix one and two, F5L, N28K and K35I. It contains a GGG linker in position 37-39 and the calcium binding motif in position 40-51. All positions are important for the interaction between the Z domain and IgG. It also contains a mutation at position 55, Q55R (numbering according to the original Z scaffold, for Zmat8 this amino acid is in position 66). The original amino acid forms hydrogen bonds to other amino acids in the original scaffold[31].

In order to challenge Zmat8 in a relevant purification setup, it was coupled to an NHS-activated matrix. The parental domain Z was coupled in a similar way and the results from the two different columns were compared. It was investigated whether polyclonal human IgG could be captured on the columns and under what conditions the captured antibodies were eluted. IgG was eluted from the Zmat8 column in a calcium dependent manner at pH 5.5 (FIG. 3a) but not on the Z column (FIG. 3b). As a control IgG was eluted from both columns by lowering the pH to 3.2, which showed that IgG was eluted with EDTA in a comparable manner to acid on the Zmat8 column. Moreover the elution profiles obtained with low pH from the Zmat8 and Z column were shown to be very similar (figure FIG. 3).

Figure 4:
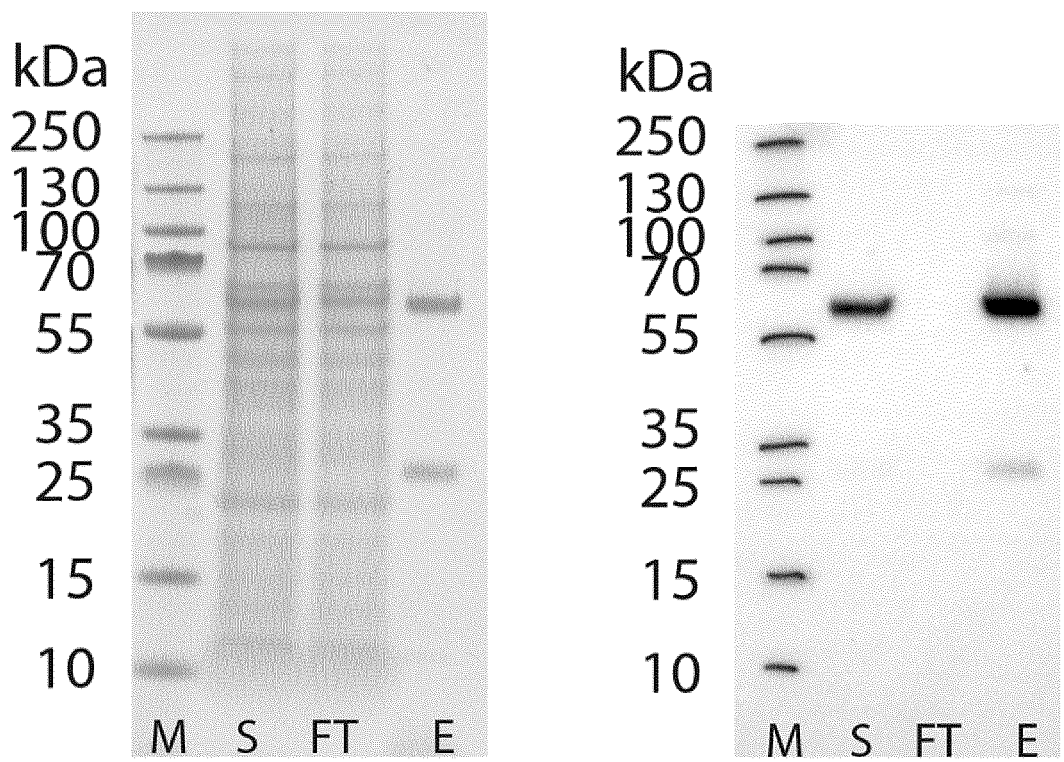

A Chinese hamster ovary (CHO) cell culture supernatant spiked with polyclonal human IgG (100 mg/l) and a CHO cell culture supernatant with produced human IgG (approx. 10 mg/l) were used for test purifications. Both supernatants were purified to high homogeneity and purity with EDTA elution after capture on the Zmat8 column, as exemplified by the supernatant with produced IgG in FIG. 4.

Experiment 2

Genes for a monomer and head to tail multimers (dimer, trimer and tetramer) of Zmat8 (SEQ ID NO 8) including a C-terminal cysteine were amplified and cloned into an expression vector. The proteins have been expressed in E. coli and purified on IgG Sepharose.

Equimolar amounts of the proteins were immobilised on an iodoacetyl resin for covalent immobilisation of cysteines (SulfoLink™ coupling resin, ThermoFisher). A large excess of polyclonal human IgG was added to the resins in a test purification set up with EDTA elution to test the binding capacity of the columns.

Materials & Methods
Resin Coupling

Covalent and irreversible immobilization of the proteins to columns was done using SulfoLink® Coupling Resin (Thermo Scientific), activated with iodoacetyl groups, via the C-terminal cysteine. Approximately 70 nmole of each protein variant, corresponding to 0.5 mg Zmat8MonoCys, 1 mg Zmat8DiCys, 1.5 mg Zmat8TriCys and 2 mg Zmat8TetCys, was diluted in coupling buffer (50 mM Tris, 5 mM EDTA, pH 8) in a total volume of 1 ml of each protein was used. Absorbance at 280 nm was measured using an Eppendorf BioPhotometer to ensure correct amounts of each protein. 0.5 M TCEP pH adjusted to 7 (Sigma) was added to a final concentration of 25 mM and incubated at room temperature for 30 min. The covalent immobilization of each protein to a 1 ml SulfoLink® Coupling Resin bed was conducted according to the manufacturer's instructions, with the addition of allowing the coupling reaction to occur in the dark, using emptied NAP-5 columns. As storage buffer, 1xTBST-C with 20% EtOH was used. The coupling degrees were determined by measuring absorbance at 280 nm of the non-coupled fractions that were collected from the columns after the coupling reaction, and comparing them with the absorbances that were measured prior to adding the protein mixture to the columns.

Purification

In order to test the capacity of the coupled resins, test purifications were conducted in triplicates. A large excess (50 mg) of pure polyclonal human IgG in 2 ml 1xTBST-C (50 mM Tris, 150 mM NaCl, 1 mM CaCl$_2$, 0.05% Tween 20, pH 7.5) was purified on each column during each test purification. The columns were pulsed with 4 ml 0.3 M HAc (pH 3.3) and 4 ml 1xTBST-C twice. The 2 ml of pure IgG was added followed by washing with 10 ml 1xTBST-C. Elution buffer (100 mM NH$_4$Ac, 100 mM EDTA, 0.05% Tween20, pH 5.5) was added in 10x300 µl fractions. The columns were washed with 3 ml 5 mM NH$_4$Ac, 1 mM CaCl$_2$ prior to a second elution with 0.3 M HAc in 10x300 µl fractions. Regeneration was conducted with 4 ml 0.3 M HAc, 20 ml 1xTBST-C and 20 ml 1xTBST with 20% EtOH. The absorbance at 280 nm was measured of each eluted fraction to determine the amount of protein eluted from the columns.

Results

The coupling efficiency to the resin were 54, 42, 48 and 49% respectively for monomer, dimer, trimer and tetramer when comparing the absorbance of the protein before coupling and the absorbance of the protein flow through after coupling.

Test purifications with excess IgG on the different columns were performed in triplicates. The average eluted amount of protein in each fraction is presented in FIG. 5. More protein is eluted from the multimeric variants of Zmat8 than the monomeric variant.

Figure 5:
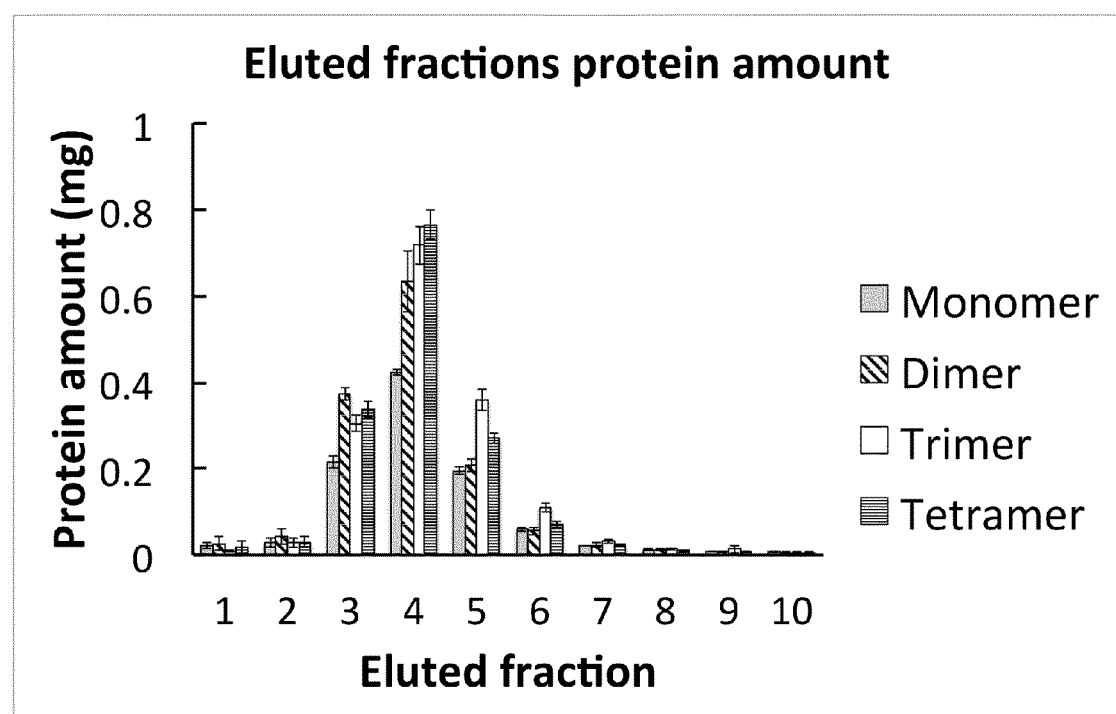
FIG. 5 is a diagram from Experiment 2 showing the average eluted amount of protein in each fraction (n=3) when a large excess of human polyclonal IgG was purified on a monomer (grey), a dimer (angled stripes) a trimer (white) or a tetramer (horizontal stripes) of Zmat8 with EDTA elution.

FIG. 5 shows the average eluted amount of protein in each fraction (n=3) when a large excess of human polyclonal IgG was purified on a monomer (grey), a dimer (angled stripes) a trimer (white) or a tetramer (horizontal stripes) of Zmat8 with EDTA elution.

The total amount of eluted protein in mg from each column and its average is presented in Table 2. No absorbance could be measured in The HAc eluted fractions, meaning elution of all protein with EDTA was successful on all the multimeric variants.

TABLE 2

The total amount of eluted protein in mg from each column in three test purifications and their average.

| | Test purification # | | | |
|---|---|---|---|---|
| | 1 | 2 | 3 | Average |
| Monomer | 1.01 | 1.02 | 0.96 | 0.99 |
| Dimer | 1.26 | 1.50 | 1.41 | 1.39 |
| Trimer | 1.66 | 1.53 | 1.60 | 1.59 |
| Tetramer | 1.60 | 1.57 | 1.45 | 1.54 |

Experiment 3

Head to tail multimers of Zmat8 with a C-terminal cysteine were coupled to 1 ml agarose based matrix in HiTrap™ columns (GE Healthcare). The variants tested were a trimer and a tetramer. The ligand amount was determined to 4.5 mg/ml for the trimer and 3.2 mg/ml for the tetramer.

The columns were used for purification on ÄKTA Pure using polyclonal human IgG. Injecting 40 mg of IgG was shown to saturate both columns. The IgG was eluted using 100 mM EDTA at pH 5.5 (FIG. 6). Elution at pH 3.3 was also performed to confirm that no IgG was left on the column. The area of the EDTA elution peaks for the two columns were compared in order to determine the purification capacity for the two variants (table 3). The tetramer could bind 1.8 times more IgG per coupled molecule and 1.3 times more IgG per binding site compared to the trimer, showing that the tetramer has a higher binding capacity than the trimer in a column purification set up.

TABLE 3

| | Coupling degree (M) | Binding sites | Area eluted IgG (mAU*ml) |
|---|---|---|---|
| Zmat8TriCys | $2.0 * 10^{-4}$ | 3 | 4900 |
| Zmat8TetCys | $1.0 * 10^{-4}$ | 4 | 4300 |

Coupling degrees in M (Mw Zmat8TriCys = 23 036 Da, Zmat8TetCys = 30 675 Da), number of binding sites and the average chromatogram peak areas (n = 3) of IgG eluted with EDTA for the trimer and tetramer of Zmat8 coupled to a purification column.

Materials and Methods

Zmat8TriCys and Zmat8TetCys were covalently immobilized via the C-terminal cysteine to agarose-based resin and packed into 1 ml HiTrap™ columns (GE Healthcare). Coupling degrees were determined through amino acid analysis. The columns were used to purify human polyclonal IgG in an ÄKTA Pure chromatography system (GE Healthcare).

The columns were pulsed with 6 column volumes (c.v.) 1xTBST-C (1xTBS (50 mM Tris, 150 mM NaCl, 0.05% Tween20, 1 mM CaCl2, pH 7.5) and 6 c.v. elution buffer (0.3 M HAc, pH 3.3 or 100 mM NH$_4$Ac, 100 mM EDTA, 0.05% Tween20, pH 5.5) before equilibration with 13 c.v. 1xTBST-C. They were then saturated with 40 mg IgG in 2 ml 1xTBST-C followed by washing with 13 c.v. 1xTBST-C and 5 c.v. 5 mM NH$_4$Ac, 1 mM CaCl$_2$. Next, 6 c.v. of elution buffer was added to the columns and the eluate was collected in fractions of 500 µl. The columns were regenerated using 3 c.v. elution buffer and 6 c.v. 1xTBST-C. In order to compare both elution buffers and both protein ligands, triplicates using each elution buffer were conducted on each column with Zmat8TriCys or Zmat8TetCys. Abs$_{280}$ chromatograms including peak areas of each purification were generated by the ÄKTA pure software.

Alkaline Stability

In order to test whether the alkaline stability of Zmat8 could be improved, mutations known to improve the alkaline stability of the original Z domain, N3A, N6A and N23T, were introduced to the molecule as well as N42D and N44D, two asparagines that are part of the calcium binding loop. Mutating position 6, 42 or 44 decreased the affinity between IgG and Zmat8 and caused leakage from the column when being purified why they were deemed unfit for further work. The N3A mutation showed no change in alkaline stability compared to Zmat8, neither a change in affinity.

Figure 7:
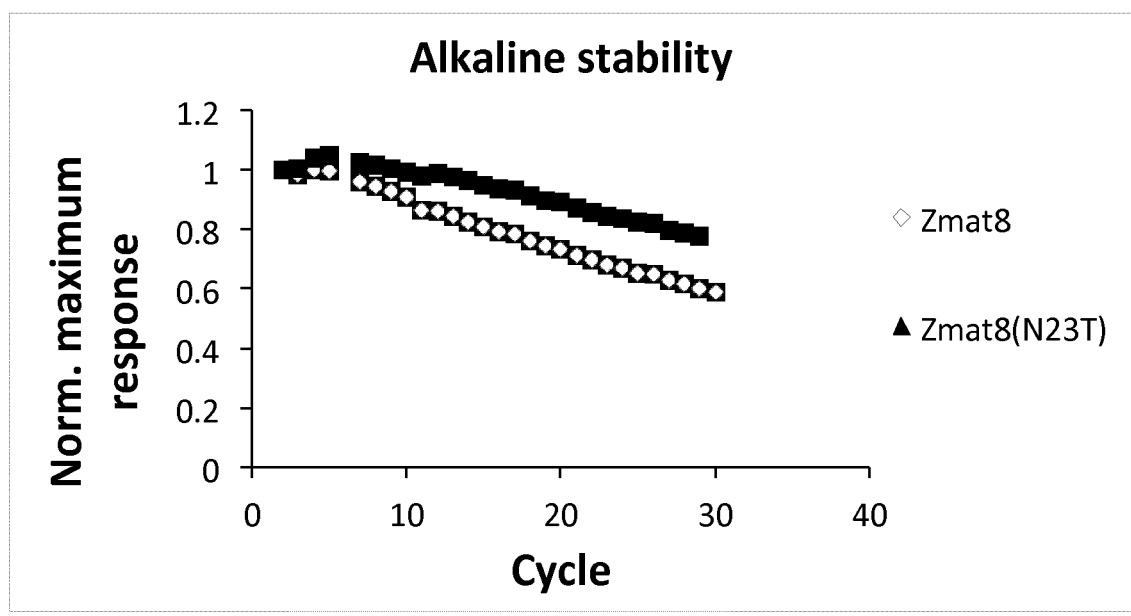
FIG. 7 shows the normalized maximum response for a set concentration of IgG flown over a surface coupled with Zmat8 or Zmat8(N23T) over 30 cycles with regeneration of the chip performed with 100 mM NaOH and 1 mM $CaCl_2$. Zmat8(N23T) shows higher alkaline stability compared to Zmat8.

To further assess the impact of N23T, Zmat8 and Zmat8 (N23T) were coupled to a Biacore chip surface. IgG was injected over the surface followed by regeneration with 100 mM NaOH and 1 mM CaCl$_2$ over 30 cycles. The maximum response for each cycle was normalized and plotted as seen in FIG. 7. The N23T mutation showed an improvement in alkaline stability compared to Zmat8.

Materials and Methods

The variants were produced using mismatch PCR and standard cloning procedures. They were sequence verified and produced in *E. coli*, purified to homogeneity verified by SDS-PAGE and MALDI-MS.

The SPR experiments were performed on a Biacore T200 (GE Healthcare). 1xHBSTC (10 mM HEPES, 150 mM NaCl, 0.05% Tween20, 1 mM CaCl$_2$) was used as running buffer. The variants were coupled to the chip surface using the immobilisation wizard aiming for 100 RU. After coupling the chip was conditioned with three blank injections and one test IgG injection with 10 mM HCl regeneration.

500 nM polyclonal human IgG was injected over the surface at 50 µl/min with 180 s association and 420 s dissociation. The surface was regenerated using 100 mM NaOH, 1 mM $CaCl_2$ at 30 µl/min for 30 s. Thirty cycles of IgG injection followed by regeneration were performed.

The data analysis was performed by looking at the maximum response level for each injection and surface. The response was normalised by dividing each response with the maximum response for the first IgG injection so that the normalised maximum response for cycle one was 1. The normalised maximum response was plotted against the cycle to see how the alkaline regeneration affected the Zmat8 variant coupled to the chip surface.

REFERENCES

1. Ecker, D. M., Jones, S. D., and Levine, H. L. (2015) The therapeutic monoclonal antibody market. *MAbs.* 7, 9-14.
2. Gagnon, P. (2012) Technology trends in antibody purification. *J Chromatogr A.* 1221, 57-70.
3. Hober, S., Nord, K., and Linhult, M. (2007) Protein A chromatography for antibody purification. *J Chromatogr B Analyt Technol Biomed Life Sci.* 848, 40-7.
4. Boström, T., Nilvebrant, J., and Hober, S., *Purification systems based on bacterial surface proteins.* 2012: INTECH Open Access Publisher.
5. Vazquez-Rey, M. and Lang, D. A. (2011) Aggregates in monoclonal antibody manufacturing processes. *Biotechnol Bioeng.* 108, 1494-508.
6. Shukla, A. A., Gupta, P., and Han, X. (2007) Protein aggregation kinetics during Protein A chromatography. Case study for an Fc fusion protein. *J Chromatogr A.* 1171, 22-8.
7. Pabst, T. M., Palmgren, R., Forss, A., Vasic, J., Fonseca, M., Thompson, C., Wang, W. K., Wang, X., and Hunter, A. K. (2014) Engineering of novel Staphylococcal Protein A ligands to enable milder elution pH and high dynamic binding capacity. *J Chromatogr A.* 1362, 180-5.
8. Gulich, S., Uhlen, M., and Hober, S. (2000) Protein engineering of an IgG-binding domain allows milder elution conditions during affinity chromatography. *J Biotechnol.* 76, 233-44.
9. Arakawa, T., Philo, J. S., Tsumoto, K., Yumioka, R., and Ejima, D. (2004) Elution of antibodies from a Protein-A column by aqueous arginine solutions. *Protein Expr Purif.* 36, 244-8.
10. Koguma, I., Yamashita, S., Sato, S., Okuyama, K., and Katakura, Y. (2013) Novel purification method of human immunoglobulin by using a thermo-responsive protein A. *J Chromatogr A.* 1305, 149-53.
11. Grabarek, Z. (2006) Structural basis for diversity of the EF-hand calcium-binding proteins. *J Mol Biol.* 359, 509-25.
12. Yanez, M., Gil-Longo, J., and Campos-Toimil, M. (2012) Calcium binding proteins. *Adv Exp Med Biol.* 740, 461-82.
13. Gifford, J. L., Walsh, M. P., and Vogel, H. J. (2007) Structures and metal-ion-binding properties of the Ca2+-binding helix-loop-helix EF-hand motifs. *Biochem J.* 405, 199-221.
14. Ye, Y., Lee, H. W., Yang, W., Shealy, S. J., Wilkins, A. L., Liu, Z. R., Torshin, I., Harrison, R., Wohlhueter, R., and Yang, J. J. (2001) Metal binding affinity and structural properties of an isolated EF-loop in a scaffold protein. *Protein Eng.* 14, 1001-13.
15. O'connell, D., LINSE, S. S., THULIN, E., and Merino, A., *Affinity tag system,* 2013, Google Patents WO2013/102684A1.
16. Marino, S. F., Shechner, D., and Regan, L. (2001) 'Morphs' (MRFs): metal-reversible folding domains for differential IgG binding. *Chem Biol.* 8, 1221-9.
17. Nilsson, B., Moks, T., Jansson, B., Abrahmsen, L., Elmblad, A., Holmgren, E., Henrichson, C., Jones, T. A., and Uhlen, M. (1987) A synthetic IgG-binding domain based on staphylococcal protein A. *Protein Eng.* 1, 107-13.
18. Wilson, M. A. and Brunger, A. T. (2000) The 1.0 A crystal structure of Ca(2+)-bound calmodulin: an analysis of disorder and implications for functionally relevant plasticity. *J Mol Biol.* 301, 1237-56.
19. Blanchard, H., Grochulski, P., Li, Y., Arthur, J. S., Davies, P. L., Elce, J. S., and Cygler, M. (1997) Structure of a calpain Ca(2+)-binding domain reveals a novel EF-hand and Ca(2+)-induced conformational changes. *Nat Struct Biol.* 4, 532-8.
20. Nagae, M., Nozawa, A., Koizumi, N., Sano, H., Hashimoto, H., Sato, M., and Shimizu, T. (2003) The crystal structure of the novel calcium-binding protein AtCBL2 from Arabidopsis thaliana. *J Biol Chem.* 278, 42240-6.
21. Kuboniwa, H., Tjandra, N., Grzesiek, S., Ren, H., Klee, C. B., and Bax, A. (1995) Solution structure of calcium-free calmodulin. *Nat Struct Biol.* 2, 768-76.
22. Ishida, H., Takahashi, K., Nakashima, K., Kumaki, Y., Nakata, M., Hikichi, K., and Yazawa, M. (2000) Solution structures of the N-terminal domain of yeast calmodulin: Ca2+-dependent conformational change and its functional implication. *Biochemistry.* 39, 13660-8.
23. Reddy Chichili, V. P., Xiao, Y., Seetharaman, J., Cummins, T. R., and Sivaraman, J. (2013) Structural basis for the modulation of the neuronal voltage-gated sodium channel NaV1.6 by calmodulin. *Sci Rep.* 3, 2435.
24. Tashiro, M., Tejero, R., Zimmerman, D. E., Celda, B., Nilsson, B., and Montelione, G. T. (1997) High-resolution solution NMR structure of the Z domain of staphylococcal protein A. *J Mol Biol.* 272, 573-90.
25. Marsden, B. J., Shaw, G. S., and Sykes, B. D. (1990) Calcium binding proteins. Elucidating the contributions to calcium affinity from an analysis of species variants and peptide fragments. *Biochem Cell Biol.* 68, 587-601.
26. Bottomley, S. P., Popplewell, A. G., Scawen, M., Wan, T., Sutton, B. J., and Gore, M. G. (1994) The stability and unfolding of an IgG binding protein based upon the B domain of protein A from Staphylococcus aureus probed by tryptophan substitution and fluorescence spectroscopy. *Protein Eng.* 7, 1463-70.
27. Chowdhury, S., Lei, H., and Duan, Y. (2005) Denatured-state ensemble and the early-stage folding of the G29A mutant of the B-domain of protein A. *J Phys Chem B.* 109, 9073-81.
28. Cedergren, L., Andersson, R., Jansson, B., Uhlen, M., and Nilsson, B. (1993) Mutational analysis of the interaction between staphylococcal protein A and human IgG1. *Protein Eng.* 6, 441-8.
29. Jendeberg, L., Persson, B., Andersson, R., Karlsson, R., Uhlen, M., and Nilsson, B. (1995) Kinetic analysis of the interaction between protein A domain variants and human Fc using plasmon resonance detection. *J Mol Recognit.* 8, 270-8.

30. Deisenhofer, J. (1981) Crystallographic refinement and atomic models of a human Fc fragment and its complex with fragment B of protein A from Staphylococcus aureus at 2.9- and 2.8-A resolution. *Biochemistry.* 20, 2361-70.
31. Feldwisch, J., Tolmachev, V., Lendel, C., Herne, N., Sjoberg, A., Larsson, B., Rosik, D., Lindqvist, E., Fant, G., Hoiden-Guthenberg, I., et al. (2010) Design of an optimized scaffold for affibody molecules. *J Mol Biol.* 398, 232-47.
32. Alm, T., Yderland, L., Nilvebrant, J., Halldin, A., and Hober, S. (2010) A small bispecific protein selected for orthogonal affinity purification. *Biotechnol J.* 5, 605-17.
33. Gronwall, C., Jonsson, A., Lindstrom, S., Gunneriusson, E., Stahl, S., and Herne, N. (2007) Selection and characterization of Affibody ligands binding to Alzheimer amyloid beta peptides. *J Biotechnol.* 128, 162-83.
34. Löfblom et al (2010), FEBS Lett 584(12):2670-80

The invention claimed is:

1. A Fc-binding polypeptide mutant of an IgG-binding polypeptide comprising the amino acid sequence selected from SEQ ID NOs: 1-9 (Zmat1-Zmat9), wherein the Fc-binding polypeptide mutant is a mutant of domain Z derived from Staphylococcus Protein A (SpA) domain B and comprises a metal binding motif inserted between helix 2 and 3 of the mutant of domain Z, wherein Fc binding occurs in the presence of a metal ion and wherein the Fc-binding polypeptide mutant optionally comprises the following Z domain mutation: N23T.

2. The Fc-binding polypeptide mutant according to claim 1, wherein the metal binding motif is calcium binding and the Fc-binding is in the presence of calcium ions.

3. The Fc-binding polypeptide mutant according to claim 1, comprising a linker before the metal binding motif.

4. The Fc-binding polypeptide mutant according to claim 1, comprising the amino acid sequence of SEQ ID NO: 8 (Zmat8).

5. The Fc-binding polypeptide mutant according to claim 1, comprising the following domain Z mutations: F5L, N28K, K35I.

6. A ligand comprising the Fc-binding polypeptide mutant according to claim 1.

7. The ligand according to claim 6, comprising the Fc-binding polypeptide mutant comprising the amino acid sequence of SEQ ID NO: 8 (Zmat8).

8. The ligand according to claim 6, wherein the ligand is a multimer selected from a dimer, trimer, tetramer, pentamer or hexamer.

9. A chromatography matrix comprising the ligand according to claim 6 or multimer thereof.

10. A polypeptide comprising the amino acid sequence selected from SEQ ID Nos:1-9 (Zmat1-Zmat9).

11. The polypeptide of claim 10, wherein the amino acid sequence is SEQ ID NO:8.

12. A method for purification of target or sample proteins, comprising binding the target or sample proteins to a the ligand according to claim 6 or multimer thereof in the presence of a metal ion; and eluting bound proteins by addition of a metal binding molecule.

13. The method according to claim 12, wherein the ligand or multimer ligand is immobilized to a solid phase.

14. The method according to claim 12, wherein the bound proteins are eluted at a pH above 4.5.

15. The method according to claim 14, where the bound proteins are eluted at pH 5-7.

16. The method according to claim 15, where the bound proteins are eluted at pH 5.4-5.6.

17. The method according to claim 12, wherein the target or sample proteins are antibodies or portions thereof.

18. The method according to claim 17, wherein the target or sample proteins are IgG.

19. The method according to claim 17, wherein the target or sample proteins are Fc-fusion proteins.

20. The method according to claim 12, wherein the elution with metal binding molecule is with a chelating agent.

21. A nucleic acid or vector encoding a polypeptide comprising the amino acid sequence selected from SEQ ID NOs: 1-9.

22. An expression vector comprising the nucleic acid or vector of claim 21.

\* \* \* \* \*

SEQUENCE LISTING

```
<160> NUMBER OF SEQ ID NOS: 11

<210> SEQ ID NO 1
<211> LENGTH: 69
<212> TYPE: PRT
<213> ORGANISM: Artificial Sequence
<220> FEATURE:
<223> OTHER INFORMATION: Zmat1

<400> SEQUENCE: 1

Val Glu Asn Lys Phe Asn Lys Glu Gln Gln Tyr Ala Phe Tyr Glu Ile
1               5                   10                  15

Leu His Leu Ala Asn Leu Asn Glu Glu Gln Arg Asn Ala Phe Ile Gln
            20                  25                  30

Ser Leu Ile Asp Gly Ser Gly Asp Thr Asn Gly Asn Gly Tyr Leu Asp
        35                  40                  45

Ala Glu Glu Ser Ala Asn Leu Leu Ala Glu Ala Lys Lys Leu Asn Asp
    50                  55                  60

Ala Gln Ala Pro Ile
65

<210> SEQ ID NO 2
<211> LENGTH: 69
<212> TYPE: PRT
<213> ORGANISM: Artificial Sequence
<220> FEATURE:
<223> OTHER INFORMATION: Zmat2

<400> SEQUENCE: 2

Val Asp Asn Lys Phe Asn Glu Glu Gln Gln Asn Ala Phe Phe Glu Ile
1               5                   10                  15

Leu His Leu Pro Asn Leu Asn Glu Glu Gln Arg Asn Ala Phe Ile Gln
            20                  25                  30

Ser Leu Ile Asp Gly Ser Gly Asp Thr Asn Gly Asn Gly Tyr Leu Asp
        35                  40                  45

Ala Glu Glu Ser Ala Asn Leu Leu Ala Glu Ala Arg Lys Leu Asn Asp
    50                  55                  60

Ala Gln Ala Pro Lys
65

<210> SEQ ID NO 3
<211> LENGTH: 69
<212> TYPE: PRT
<213> ORGANISM: Artificial Sequence
<220> FEATURE:
<223> OTHER INFORMATION: Zmat3

<400> SEQUENCE: 3

Val Asp Asn Lys Phe Asn Lys Glu Gln Gln Asn Ala Phe Tyr Glu Ile
1               5                   10                  15

Leu Arg Leu Pro Asn Leu Asn Glu Glu Gln Arg Asn Ala Phe Ile Gln
```

```
            20                  25                  30

Ser Leu Ile Asp Gly Ser Gly Asp Thr Asn Arg Asn Gly Tyr Leu Asp
        35                  40                  45

Ala Glu Glu Ser Ala Asn Leu Leu Ala Glu Ala Lys Lys Leu Asn Asp
    50                  55                  60

Ala Arg Ala Pro Lys
65

<210> SEQ ID NO 4
<211> LENGTH: 69
<212> TYPE: PRT
<213> ORGANISM: Artificial Sequence
<220> FEATURE:
<223> OTHER INFORMATION: Zmat4

<400> SEQUENCE: 4

Gly Asp Asn Lys Phe Asn Lys Glu Gln Gln Asn Ala Phe Tyr Glu Ile
1               5                   10                  15

Leu Gln Leu Pro Asn Leu Asn Glu Glu Gln Arg Asn Ala Phe Ile Gln
            20                  25                  30

Ser Leu Asn Asp Gly Gly Gly Asp Thr Asn Gly Asn Gly Tyr Leu Asp
        35                  40                  45

Ala Glu Glu Ser Ala Asn Leu Leu Ala Glu Ala Lys Lys Leu Asn Asp
    50                  55                  60

Ala Gln Ala Pro Lys
65

<210> SEQ ID NO 5
<211> LENGTH: 69
<212> TYPE: PRT
<213> ORGANISM: Artificial Sequence
<220> FEATURE:
<223> OTHER INFORMATION: Zmat5

<400> SEQUENCE: 5

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg His Ala Phe Ile Gln
            20                  25                  30

Ser Leu Ile Asp Gly Gly Gly Asp Thr Asn Gly Asn Gly Tyr Leu Asp
        35                  40                  45

Ala Glu Glu Ser Ala Asn Leu Leu Ala Glu Ala Lys Lys Leu Asn Asp
    50                  55                  60

Ala Gln Ala Pro Lys
65

<210> SEQ ID NO 6
<211> LENGTH: 69
<212> TYPE: PRT
<213> ORGANISM: Artificial Sequence
<220> FEATURE:
<223> OTHER INFORMATION: Zmat6

<400> SEQUENCE: 6

Val Asp Asn Lys Ile Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Asn Asp Gly Gly Gly Asp Thr Asn Gly Asn Gly Tyr Leu Asp
        35                  40                  45
```

Ala Glu Glu Ser Ala Asn Leu Ile Ala Glu Ala Lys Lys Leu Asn Asp
        50                  55                  60

Ala Gln Ala Pro Lys
65

<210> SEQ ID NO 7
<211> LENGTH: 68
<212> TYPE: PRT
<213> ORGANISM: Artificial Sequence
<220> FEATURE:
<223> OTHER INFORMATION: Zmat7

<400> SEQUENCE: 7

Val Asp Asn Lys Leu Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Ile Asp Gly Gly Gly Asp Thr Asn Gly Asn Gly Tyr Leu Asp
        35                  40                  45

Ala Glu Glu Ser Ala Asn Leu Leu Ala Glu Ala Lys Lys Leu Asn Asp
        50                  55                  60

Ala Gln Ala Pro
65

<210> SEQ ID NO 8
<211> LENGTH: 69
<212> TYPE: PRT
<213> ORGANISM: Artificial Sequence
<220> FEATURE:
<223> OTHER INFORMATION: Zmat8

<400> SEQUENCE: 8

Val Asp Asn Lys Leu Asn Lys Glu Gln Gln Asn Ala Phe Tyr Glu Ile
1               5                   10                  15

Leu His Leu Pro Asn Leu Asn Glu Glu Gln Arg Lys Ala Phe Ile Gln
            20                  25                  30

Ser Leu Ile Asp Gly Gly Gly Asp Thr Asn Gly Asn Gly Tyr Leu Asp
        35                  40                  45

Ala Glu Glu Ser Ala Asn Leu Leu Ala Glu Ala Lys Lys Leu Asn Asp
        50                  55                  60

Ala Arg Ala Pro Lys
65

<210> SEQ ID NO 9
<211> LENGTH: 69
<212> TYPE: PRT
<213> ORGANISM: Artificial Sequence
<220> FEATURE:
<223> OTHER INFORMATION: Zmat9

<400> SEQUENCE: 9

Val Asp Glu Lys Phe Asn Lys Glu Gln Gln Asn Ala Phe Tyr Glu Ile
1               5                   10                  15

Leu Tyr Leu Pro Asn Leu Asn Glu Glu Gln Arg Asn Ala Phe Ile Arg
            20                  25                  30

Ser Leu Ile Asp Gly Gly Gly Asp Thr Asn Gly Asn Gly Tyr Leu Asp
        35                  40                  45

Ala Glu Glu Ser Ala Asn Leu Leu Ala Glu Ala Lys Lys Leu Asn Asp
        50                  55                  60

```
Ala Gln Ala Pro Lys
65

<210> SEQ ID NO 10
<211> LENGTH: 69
<212> TYPE: PRT
<213> ORGANISM: Artificial Sequence
<220> FEATURE:
<223> OTHER INFORMATION: A5

<400> SEQUENCE: 10

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Gly Gly Gly Asp Thr Asn Gly Asn Gly Tyr Leu Asp
        35                  40                  45

Ala Glu Glu Ser Ala Asn Leu Leu Ala Glu Ala Lys Lys Leu Asn Asp
    50                  55                  60

Ala Gln Ala Pro Lys
65

<210> SEQ ID NO 11
<211> LENGTH: 12
<212> TYPE: PRT
<213> ORGANISM: Artificial Sequence
<220> FEATURE:
<223> OTHER INFORMATION: Calmodulin

<400> SEQUENCE: 11

Asp Lys Asp Gly Asp Gly Thr Ile Thr Thr Lys Glu
1               5                   10
```